(12) United States Patent
Atsumori et al.

(10) Patent No.: US 9,706,955 B2
(45) Date of Patent: Jul. 18, 2017

(54) BIOLOGICAL STATE ASSESSMENT DEVICE AND PROGRAM THEREFOR

(75) Inventors: Hirokazu Atsumori, Tokyo (JP); Masashi Kiguchi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 171 days.

(21) Appl. No.: 14/408,644

(22) PCT Filed: Jun. 21, 2012

(86) PCT No.: PCT/JP2012/065868
§ 371 (c)(1),
(2), (4) Date: Jan. 21, 2015

(87) PCT Pub. No.: WO2013/190678
PCT Pub. Date: Dec. 27, 2013

(65) Prior Publication Data
US 2015/0297126 A1    Oct. 22, 2015

(51) Int. Cl.
*A61B 5/1455* (2006.01)
*A61B 5/00* (2006.01)
*A61B 5/145* (2006.01)
*G06N 5/04* (2006.01)
*A61B 5/16* (2006.01)

(52) U.S. Cl.
CPC ...... *A61B 5/14553* (2013.01); *A61B 5/14546* (2013.01); *A61B 5/14552* (2013.01); *A61B 5/165* (2013.01); *A61B 5/486* (2013.01); *A61B 5/7225* (2013.01); *A61B 5/7246* (2013.01); *A61B 5/7278* (2013.01); *A61B 5/7475* (2013.01); *G06N 5/04* (2013.01); *A61B 5/742* (2013.01); *A61B 5/743* (2013.01); *A61B 5/7435* (2013.01); *A61B 2505/09* (2013.01);
(Continued)

(58) Field of Classification Search
CPC .............. A61B 5/14551; A61B 5/1455; A61B 5/14553; A61B 5/0059; A61B 5/0075
See application file for complete search history.

(56) References Cited

U.S. PATENT DOCUMENTS

2007/0083097 A1*  4/2007  Fujiwara .............. A61B 5/0059
                                                        600/407
2011/0319784 A1* 12/2011  Nakagawa ........... A61B 5/0476
                                                        600/544

FOREIGN PATENT DOCUMENTS

JP        09-098972 A       4/1997
JP        2009-285000 A    12/2009
(Continued)

*Primary Examiner* — Tse Chen
*Assistant Examiner* — Yoojin Lee
(74) *Attorney, Agent, or Firm* — Mattingly & Malur, PC

(57) ABSTRACT

Provided is a biological state assessment device for assessing biological state, such as mood or emotions, using non-invasive biophotonic measurement technology. The present invention includes a light irradiation unit (1041), a light-receiving unit (1061), and an inputting means (112). A subject (800) is presented with a plurality of different problems (first problem, second problem), and a biological signal in the interior of the subject is calculated from the intensity of light received by the light-receiving unit (1061). Subjective information about the subject is accepted by the inputting means (112). The difference is calculated between the subjective information and the relative value of the biological signal of the measurement point for the first problem and the biological signal of the measurement point for the second problem, and the result is displayed.

4 Claims, 24 Drawing Sheets

(52) U.S. Cl.
CPC .............. *A61B 2560/0475* (2013.01); *A61B 2562/0238* (2013.01)

(56) References Cited

FOREIGN PATENT DOCUMENTS

| | | |
|---|---|---|
| JP | 2011-238215 A | 11/2011 |
| JP | 2012-075727 A | 4/2012 |
| WO | 2011/065237 A1 | 6/2011 |

* cited by examiner

FIG. 5

INPUT APPROPRIATE SCORE FIT TO YOUR PRESENT MOOD

| SUBJECTIVE SCORE | DETERMINATION CRITERIA |
|---|---|
| 100-120 | TALKATIVE, RESTLESS, EXCITED |
| 80-120 | REFRESHED, ACTIVE, PLEASANT, RATHER HIGH MOOD |
| 60-80 | ENTHUSIASTIC, PLEASANT TO GO OUT, ENABLE TO DO HOBBY |
| 40-60 | CALM, SETTLED, NORMALLY INTERESTED TO DO ACTIVITY |
| 20-40 | DEPRESSED, UNEASY, IRRITATED, IMPATIENT, WEARY |
| 0-20 | WORST DEPRESSED STATE, ALWAYS LYING |

PRESENT MOOD IS AT SCORE OF 65 — 65 — OK

FIG. 6

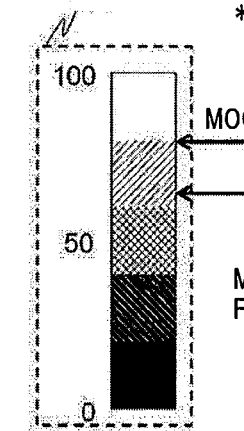

| ID | Date, time | Act_1 | Act_2 | Mood_index | Mood_sub |
|---|---|---|---|---|---|
| 001 | 2012/1/1 10:00:00 | 0.21 | 0.28 | 57.1 | 65 |
| 001 | 2012/1/8 11:58:00 | 0.15 | 0.13 | 46.4 | 50 |
| 001 | 2012/1/20 17:21:49 | 0.30 | 0.12 | 28.6 | 40 |
| ... | | | | | ... |
| 023 | 2012/1/15 20:19:33 | 0.36 | 0.19 | 34.5 | 35 |
| 023 | 2012/2/28 19:34:15 | 0.28 | 0.22 | 44.0 | 45 |
| ... | | | | | ... |

FIG. 30
(A)
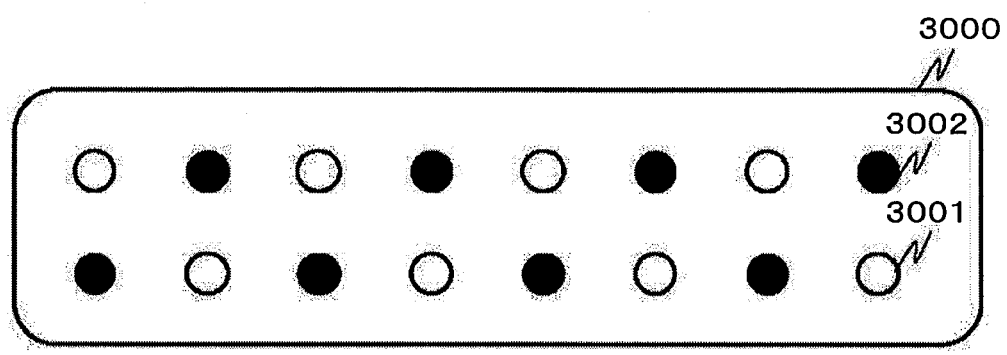
(B)
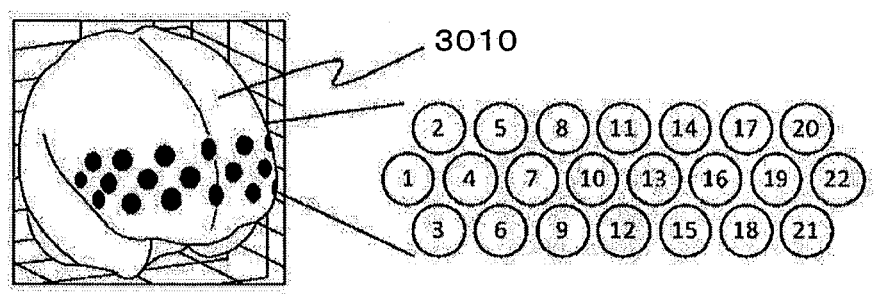

FIG. 31
(A)
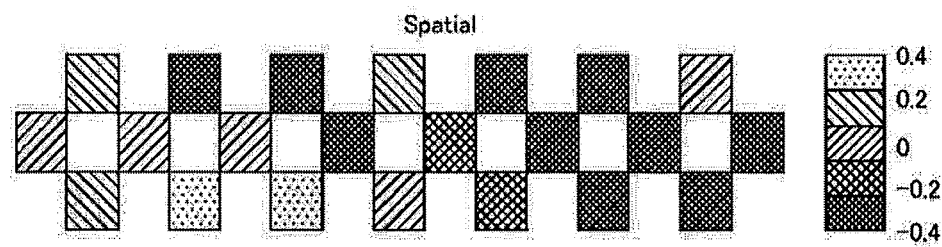
(B)
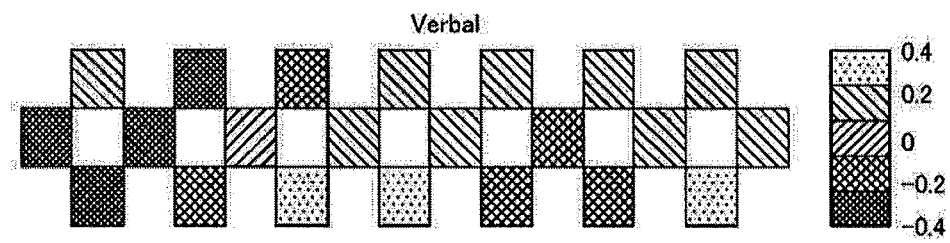
(C)
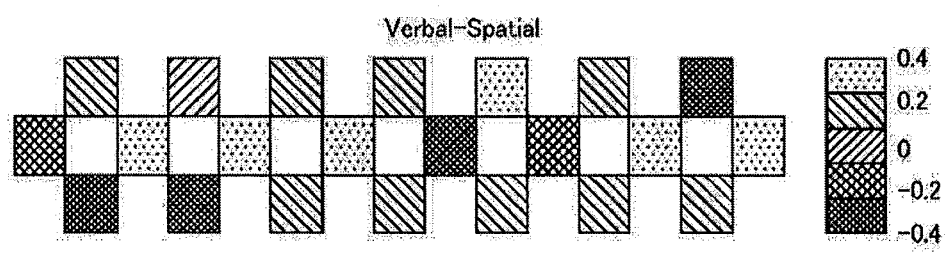

FIG. 32
(A)
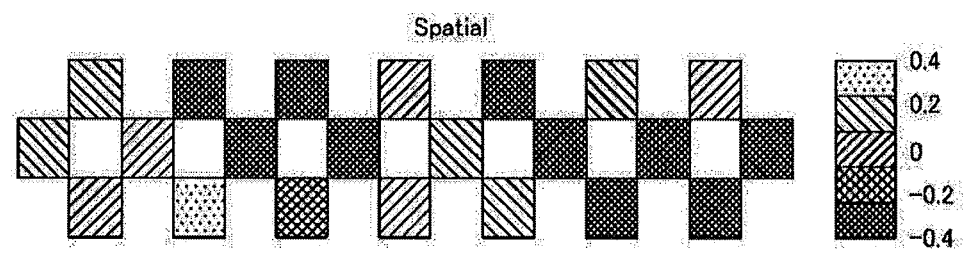
(B)
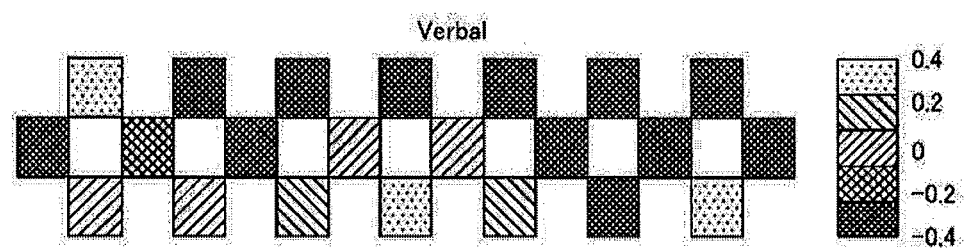
(C)
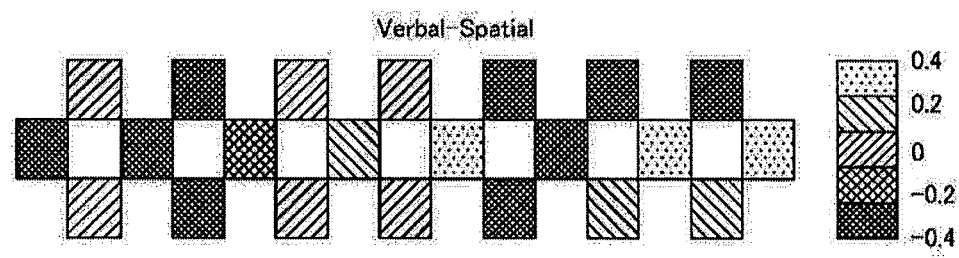

FIG. 33
(A)
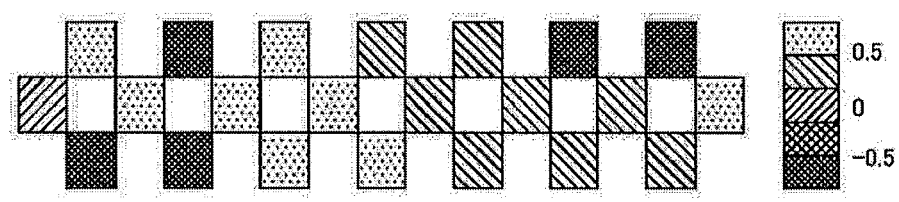
(B)
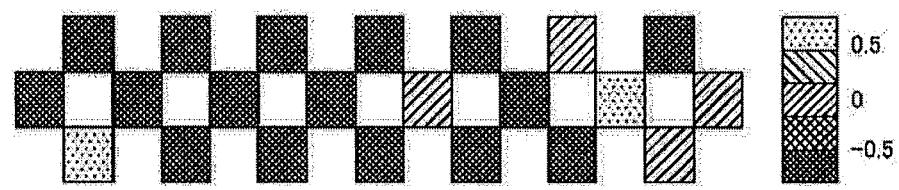

BIOLOGICAL STATE ASSESSMENT DEVICE AND PROGRAM THEREFOR

TECHNICAL FIELD

The present invention relates to a biological state assessment device that assesses the biological state of a subject based on the measurement data of a biophotonic measurement device.

BACKGROUND ART

In these years, the number of people with mental disorders is increasing, and it becomes important to appropriately grasp the mental and physical health states of individuals. To acquire and manage the mental and physical states, for example, Patent Literature 1 describes a technique which acquires the health states (sensible data) that an individual subjectively feels and the time or speed (performance data) that the individual do a certain cognitive task, and accumulates and displays those data. According to this method, it is expected that such sensible and performance data lead to an early detection of an abnormality such as the individual's indisposition or mental failure. However, the method does not directly measure mental and physical complaints, and it is difficult to eliminate the possibility that items of sensible data derived from subjective answers are greatly varied depending on individuals.

On the other hand, Patent Literature 2, for example, describes a biophotonic measurement device which visualizes two-dimensional images of information inside a living body by measuring the living body using light at a plurality of wavelengths in visible to infrared region. In the biophotonic measurement device described in this Patent Literature, lights are generated by semiconductor lasers, the generated lights are guided through optical fiber bundles, a plurality of places of a subject are irradiated with the lights, lights transmitted through or reflected off the inside of the living body are received at a plurality of places of the living body, the received lights are guided to and detected at photodiodes through another optical fiber bundles, the lights is converted into living body information such as blood circulation, hemodynamic responses, and changes in haemoglobin concentration from the detected lights, and this living body information is formed in a two-dimensional image. Since such a biophotonic measurement device has the characteristics that the device is noninvasive and low constraint to living bodies, the device is suited to the assessment of an individual's mental state and living body information under a usual environment as compared with a large scale measurement technique such as functional magnetic resonance imaging (fMRI).

Patent Literature 3, for example, describes a method for assessing a mental state and living body information under a usual environment using this biophotonic measurement device. The method described in Patent Literature 3 is in that a verbal working memory task (a task that requires a phonological loop), which uses a human working memory function, and a nonverbal working memory task (a task that requires no phonological loop) are given and frontal lobe activities in association with the memorization, retention, and recollection of the working memory tasks are measured by a biophotonic measurement technique. For the characteristics of the frontal lobe activities shown in Patent Literature 3, the frontal lobe activities in association with the memorization and retention of the verbal working memory task have a negative correlation with a score of "depression-dejection" (POMS_D) obtained by a standardized short form of the Profile of Mood State (POMS) questionnaire, whereas the frontal lobe activities have a low correlation with recollection. On the other hand, the frontal lobe activities in association with the nonverbal working memory task have no significant correlation with POMS_D. Both working memory tasks have different objects but the memorization and retention features are identical, therefore, relative frontal lobe activities from the verbal and nonverbal working memory tasks are proposed to express quantitative values that have the relationship to mood among subjects. This method has advantages in that it does not need to induce any change in mood prior to measurement and uses a low constraint and noninvasive biophotonic measurement technique. In other words, with the use of the method, it is expected to implement a mood self-check system applicable to mental healthcare by directly acquiring quantitative values reflecting a usual mod state without any stimuli inducing changes in mood.

CITATION LIST

Patent Literature

Patent Literature 1: Japanese Unexamined Patent Application Publication No. 2011-238215
Patent Literature 2: Japanese Unexamined Patent Application Publication No. 9-98972
Patent Literature 3: Japanese Unexamined Patent Application Publication No. 2009-285000

SUMMARY OF INVENTION

Technical Problem

The biophotonic measurement technique that visualizes brain activities is expected to provide an application that gives information about individual's mental states such as mood or emotion, and the technique can be used under a usual environment as compared with a large scale brain functional imaging technique such as fMRI. Moreover, a method has been proposed in which biological signals reflecting a plurality of types of cognitive tasks are acquired using the biophotonic measurement technique and the state of a usual mood is assessed. This method is expected to be applicable to assessment of mood that is not dependent on subjectivity. However, there is no method expressing the difference or the relationship between objective information about the mood state obtained by the biophotonic measurement technique and subjective information that the subject feels.

It is an object of the present invention to provide a biological state assessment device that assesses biological state by quantifying a gap or a matching degree between objective information about a biological signal measured under a usual environment and subjective information that a subject feels.

Solution to Problem

In order to solve the problem, the present invention has configurations described in claims, for example.

An example of a biological state assessment device according to the present invention is a biological state assessment device including: one or a plurality of irradiation units configured to irradiate a subject with light; one or a plurality of light receiving units configured to detect light transmitted through or reflected off the subject; a display unit configured to display a plurality of different tasks to the subject; an operating unit configured to show the task on the display unit and calculate a biological signal in an inside of the subject from intensity of light received at the light receiving unit; a storage unit configured to store the biological signal; and an input unit configured to accept an input of subjective information about the subject. In the biological state assessment device, the operating unit calculates and displays a difference between a relative value of biological signals with respect to the plurality of the tasks and the subjective information.

Moreover, an example of a program according to the present invention is a program that causes a biophotonic measurement device to operate as a biological state assessment device, the biophotonic measurement device including: one or a plurality of irradiation units configured to irradiate a subject with light; one or a plurality of light receiving units configured to detect light transmitted through or reflected off the subject; a display unit configured to display a plurality of different tasks to the subject; an operating unit configured to show the task on the display unit and calculate a biological signal in an inside of the subject from intensity of light received at the light receiving unit; a storage unit configured to store the biological signal; and an input unit, the program causing the operating unit formed of a computer to function to calculate and display a difference between a relative value of biological signals with respect to the plurality of the tasks and subjective information about the subject inputted from the input unit.

Advantageous Effects of Invention

According to the present invention, it is possible to objectively digitize a gap or a matching degree between objective information about a biological signal measured under a usual environment and subjective information that a subject feels.

Moreover, with the configuration in which the calculated result is stored on the storage unit, it is possible to analyze and display successive changes in biological state based on stored data.

BRIEF DESCRIPTION OF DRAWINGS

FIG. 5 is a diagram of an exemplary display for acquiring subjective information about a subject.

FIG. 6 is a diagram of an exemplary display of an assessment result.

FIGS. 30(A) and 30(B) are diagrams of biophotonic measurement.

FIGS. 31(A), 31(B) and 31(C) are diagrams of a correlation with a psychologist score.

FIGS. 32(A), 32(B) and 32(C) are diagrams of a correlation with a subjective score.

FIGS. 33(A) and 33(B) are diagrams of the correlation between Act(V-S) and a subjective score.

DESCRIPTION OF EMBODIMENTS

In the following, the description of embodiments of the present invention will be described in detail with reference to the drawings. In the following example, with the use of the biophotonic measurement technique, objective living body information obtained from measured results and subjective information that the subject feels are acquired, and the difference or correlation between them are displayed. For the outlines, following new findings are used that the deviation between objective mood information obtained from a brain activity signal reflecting the memorization and retention of working memories and subjective mood information that a subject feels relates to how the subject recovers from mental illness such as a depressive disorder.

Subjects targeted for assessment are people who are working on rehabilitation at a special facility among people who leave or temporarily leave from their work because of mental illness such as depressive disorders, for example. A plurality of subjects was continuously subjected to measurements below, and findings to solve the problem were obtained.

<Biophotonic Measurement>

As illustrated in FIG. 30(A), a biophotonic measurement probe 3000 having an alternating 2×8 arrangement of eight irradiation points 3001 and eight detection points 3002 is attached to a frontal lobe region, and haemoglobin (Hb) signals are acquired as brain activity data from 22 measurement channels (ch). At this time, the positions of the measurement points on a cerebral cortex surface 3010 are located as illustrated in FIG. 30(B), and the channel numbers of the measurement points are designated from one to 22. Two types of tasks, a spatial working memory task and a verbal working memory task, are given to a subject, and brain activities to the tasks are assessed.

Figure 3:
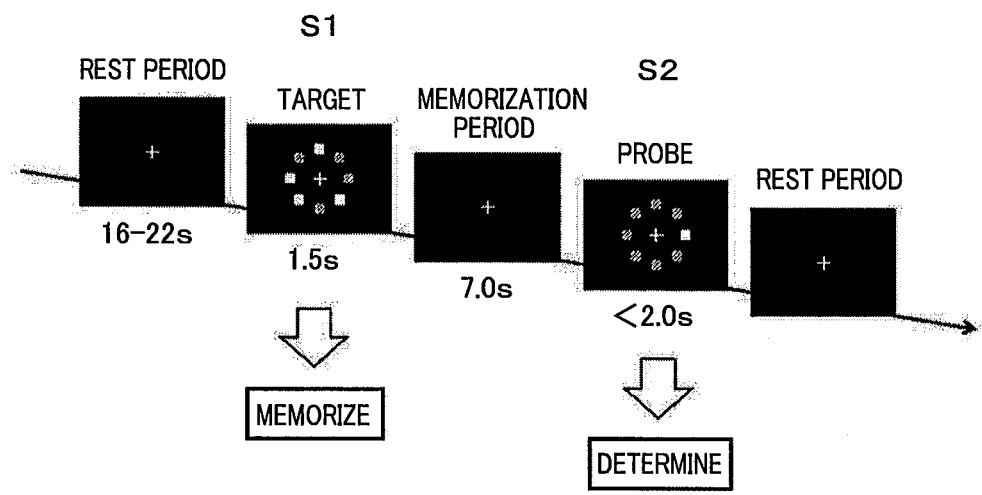
FIG. 3 is a diagram of an exemplary spatial working memory task.

The outline of the spatial working memory task is illustrated in FIG. 3. A target image (S1) is shown for 1.5 seconds. The target image includes white squares at four or two places, and the others are gray squares among eight squares disposed around the center of a fixation point. After a lapse of seven seconds, a probe image (S2) is shown. The probe image has one white square among eight squares. The subject is taught to memorize the positions of the white squares on the image S1 first shown and to determine whether the white square on the image S2 is matched with any one of the memorized positions of the white squares.

Figure 4:
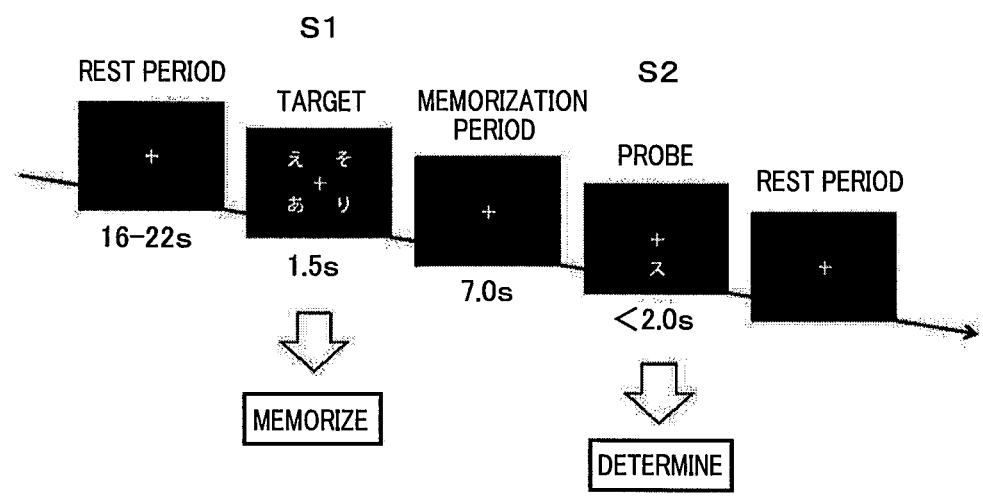
FIG. 4 is a diagram of an exemplary verbal working memory task.

The outline of the verbal working memory task is illustrated in FIG. 4. A target image (S1) is shown for 1.5 seconds. The target image (S1) includes hiragana characters displayed at four or two places around the center of a fixation point. After a lapse of seven seconds, a probe image (S2) having a katakana character is shown. The subject memorizes the characters on the first image S1 and to determine whether the katakana character on S2 subsequently shown is matched with any one of the characters first memorized. By using different types of kana characters in S1 and S2, the subject memorizes phonological information, not form information of the character.

To both of the spatial working memory task and the verbal working memory task, the subject gives an answer by pressing down a button on an input unit such as a keyboard, a controller, and a mouse.

In analysis, oxygenated and deoxygenated hemoglobin signals are calculated from time series data measured at each channel of each subject. A period of 8.5 seconds between the presentation of the first image (S1) for the working memory task and the presentation of the second image (S2) is defined as a task period. A period of 25.5 seconds including a period of one second before the task period and a period of 16 seconds after the task period is defined as a single block. Data in each block is baseline-corrected with a line which is fitted for the first one second and the last four seconds in each block. It is without saying that a time period defined as a single block is not limited to the description above and the length of a time period for the task and a time period for acquisition before and after a task can be appropriately changed.

<Questionnaire>

In order to assess the correlation between the brain activity of the working memory tasks described above and a mood state of the subject, the mood state score was acquired using a mood chart to assess the mood state. This mood chart quantifies the state of the subject's mood such as depression, willingness, and an emotional high by a score ranging from zero (the depressed state) to 120 (restless, excited). The subject records scores based on the mood chart three times a week at the special facility that supports reinstatement. Here, this is called "a subjective score". Moreover, clinical psychologists who manage and carry out reinstatement training observe how the subject spends a day, and objectively record a score of the mood chart based on the observed result. This is called "a psychologist score". The correlation of the hemoglobin signals with both "the subjective score" and "the psychologist score" expressing the mood state of the subject was assessed.

<Results>

In the investigation of the hemoglobin signals, the amplitude of a brain activity (Act) is defined as the mean value of oxygenated hemoglobin signals in a period from five seconds to 8.5 seconds after the onset of the presentation of S1, and the correlation between the Act and the subjective and psychologist scores was investigated. The results show that the mean correlation coefficient between Act(S) for the spatial working task and the psychologist score is negative (FIG. 31(A)). Moreover, it was found that there is a positive correlation between Act(V) for the verbal working memory task and the psychologist score (FIG. 31(B)). Based on this result, the difference (Act(V-S)) between Act(V) for the verbal working memory task and Act(S) for the spatial working memory task was defined by (Equation 1), and a correlation with the psychologist score was confirmed. As a result, it was revealed that Act(V-S) expresses the positive correlation with the psychologist score (FIG. 31(C)).

$$Act(V-S) = \frac{Act(V) - Act(S)}{|Act(V)| + |Act(S)|} \qquad \text{[Equation 1]}$$

Figure 34:
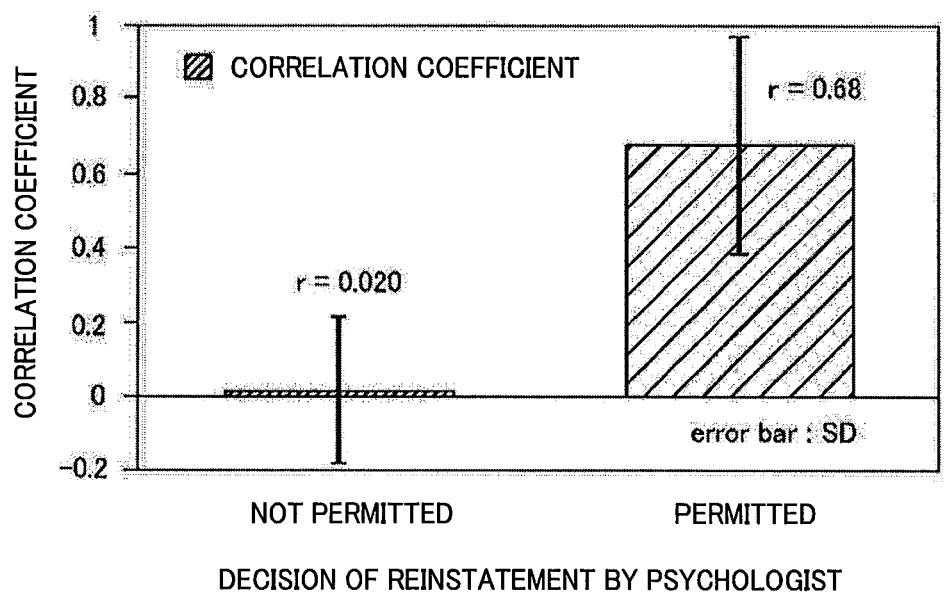
FIG. 34 is a diagram of the relationship between the decision of reinstatement by a psychologist and a correlation coefficient.

On the other hand, it was not found that the subjective score has a clear tendency like the psychologist score (FIGS. 32(A), 32(B), and 32(C)). The results above show that the difference (Act(V-S)) in the brain activity value between the verbal and spatial working memory tasks measured using biophotonic measurement expresses the psychologist score objectively described by the clinical psychologist. On the other hand, it is observed that the subjective score measured by the subject him/herself deviates from the brain activity or the psychologist score depending on subjects and the times, and it is likely that subjective information does not always correctly reflect the mood. Therefore, subjects were separated into two groups according to the deviation between the psychologist score and the subjective score, and the mean correlation coefficient of Act(V-S) with the subjective score for each group was calculated. It was observed that the group with a small deviation has a tendency of a positive correlation similar to the psychologist score (FIG. 33(A)) whereas the group with a large deviation has an opposite tendency (FIG. 33(B)). Moreover, Act(V-S) and the subjective scores of the individual subjects are separated into two periods according to the process of recovery based on the opinion of the clinical psychologist. It was revealed that the positive correlation is shown between Act(V-S) and the subjective score at the appropriate period for return-to-work which the clinical psychologists judged, whereas no clear correlation is observed at the inappropriate period for return-to-work (FIG. 34).

The results above show that the correlation coefficient and the matching degree between Act(V-S) and the subjective score are indicators to objectively grasp the state of the subject him/herself and give criteria to judge the recovery stage from a depressive disorder, for example. As described above, it is a novel method to assess the state of subject by quantifying the relationship between living body information obtained by the biophotonic measurement technique and subjective information of the subject him/herself.

Based on the findings described above, specific configurations and procedures of a biological state assessment device will be described below as embodiments.

First Embodiment

Figure 1:
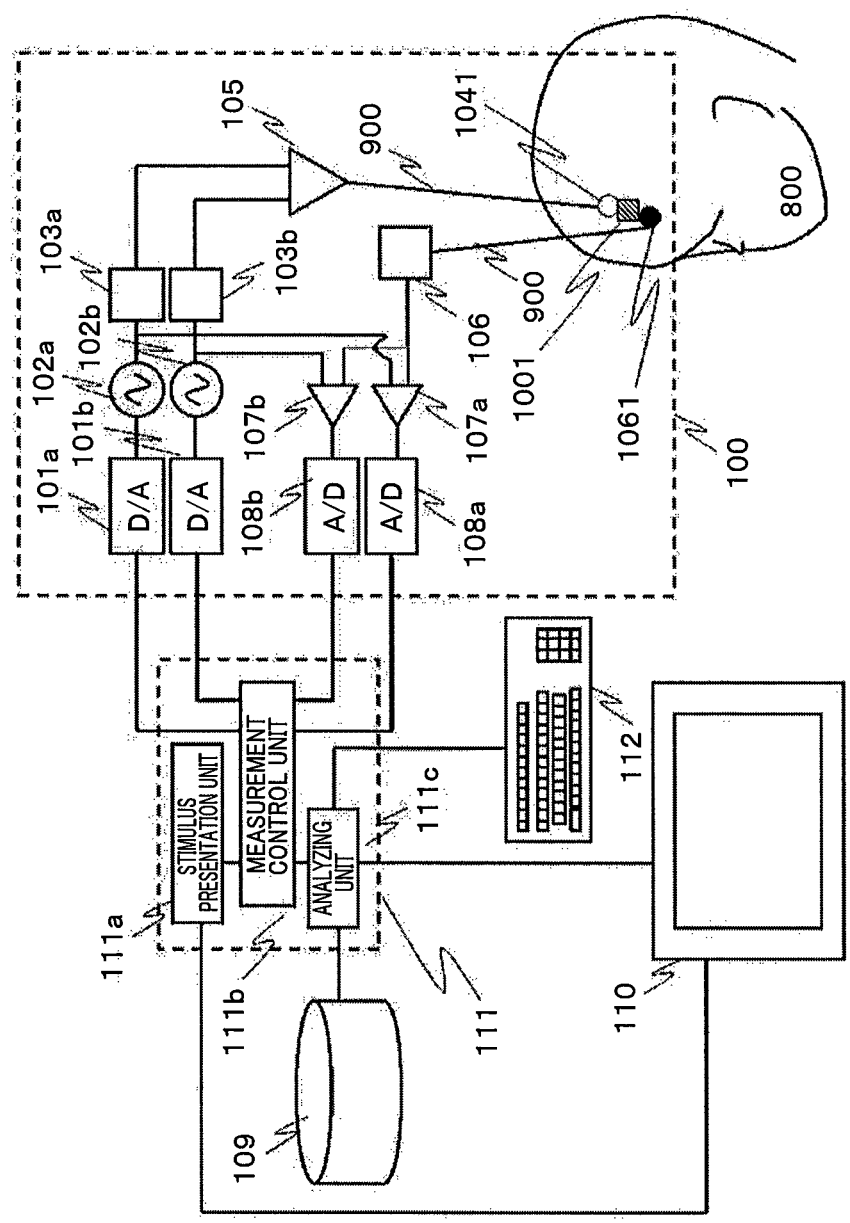
FIG. 1 is a schematic block diagram of a biological state assessment device according to a first embodiment of the present invention.

FIG. 1 is a schematic block diagram of a biological state assessment device. The biological state assessment device according to this embodiment includes a biophotonic measurement unit 100 that irradiates a subject with light and detects light transmitted through or reflected off the subject for biophotonic measurement, a display unit 110 that shows a stimulus to the subject and displays a biophotonic measurement result, an operating unit 111 that shows a stimulus on the display unit 110, gives various manners of control to the biophotonic measurement unit 100, and analyzes and displays the biophotonic measurement result on the display unit 110, an input unit 112 that accepts inputs of subjective information about the subject and answers to tasks analyzed at the operating unit 111 and various items of information necessary for analysis, and a storage unit 109 that stores the biophotonic measurement result and information about the shown tasks.

Here, the operating unit 111 includes a stimulus presentation unit 111a that shows a stimulus on the display unit 110, a measurement control unit 111b that gives various manners of control to the biophotonic measurement unit 100, and an analyzing unit 111c that analyzes and displays the biophotonic measurement result on the display unit 110. Moreover, the biophotonic measurement unit 100 is a unit that emits light at two different wavelengths in wavelengths ranging from about 600 to 900 nm, which are highly transmitted through a living body. More specifically, the biophotonic measurement unit 100 includes digital-to-analog converters 101a and 101b that convert digital signals D1a and D1b sent from the measurement control unit 111b into analog signals A1a and A1b, modulators 102a and 102b that modulate the analog signals A1a and A1b at predetermined different frequencies F1a and F1b and generate light source driving signals L1a and L1b, light sources 103a and 103b that emit light at different wavelengths based on the light source driving signals L1a and L1b such as a laser diode and an LED, an optical mixer 105 that mixes light emitted from the light sources 103a and 103b, an optical fiber bundles 900 that guides the light mixed at the optical mixer 105 to a subject, an irradiation unit 1041 that emits light guided thorough the optical fiber bundles 900 to the subject, a light receiving unit 1061 that receives light transmitted or reflected off the inside of the subject in the light emitted from the irradiation unit 1041, a measurement point 1001 that is formed at nearly a middle point between a combination of the irradiation unit 1041 and the light receiving unit 1061, a photodetector 106 that detects the light received at the light receiving unit 1061 and guided through the optical fiber bundles 900 such as a silicon photodiode, an avalanche photodiode, and a photomultiplier, lock-in amplifiers 107a and 107b that subject an analog signal A2 outputted from the photodetector 106 to lock-in processing at the different frequencies F1a and F1b, and analog-to-digital converters 108a and 108b that convert the analog signals A3a and A3b into digital signals D3a and D3b, respectively, and sends the signals to the measurement control unit 111b.

Figure 2:
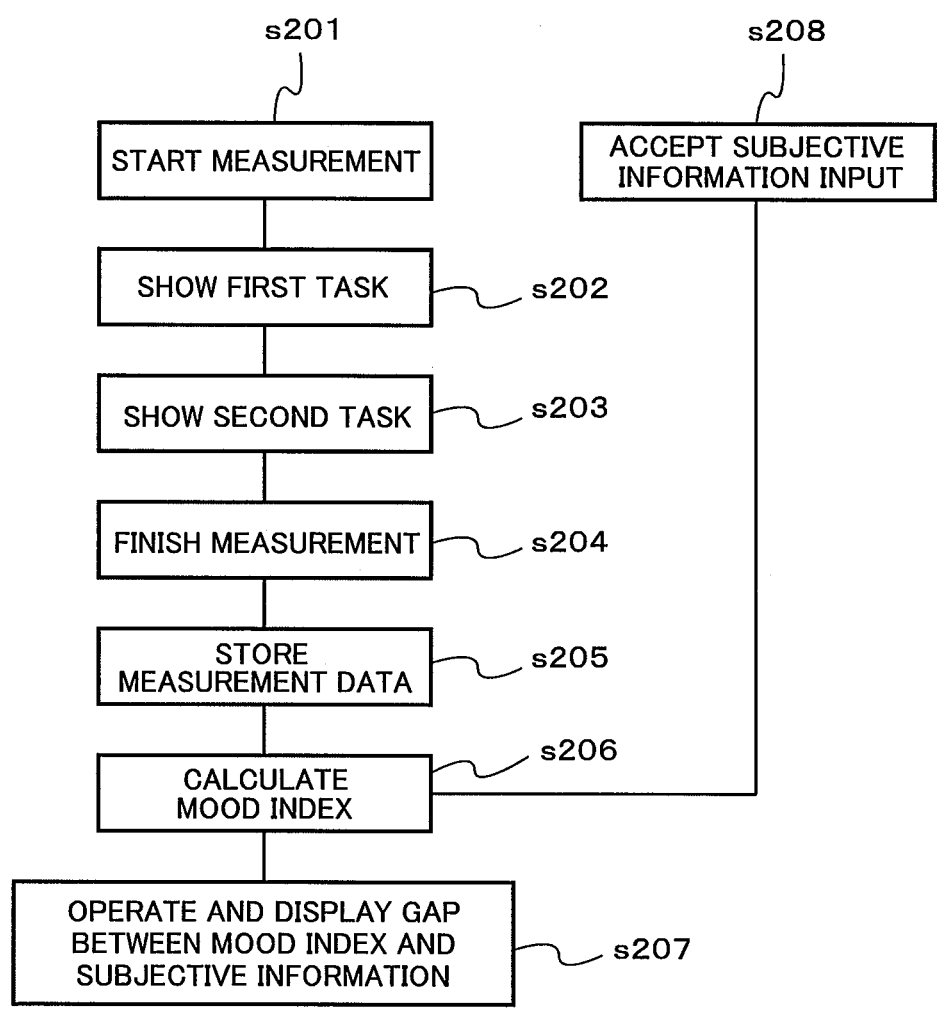
FIG. 2 is a flowchart of the process of the biological state assessment device according to the first embodiment of the present invention.

In the schematic configuration, the biological state assessment device according to the embodiment carries on processes according to a flowchart in FIG. 2. First, in Step s201, according to the control of the measurement control unit 111b of the operating unit 111, the irradiation unit 1041 starts to irradiate a subject 800 with light, and the light receiving unit 1061 starts to receive the light transmitted through or reflected off the inside of the subject 800, and acquires a biological signal from the measurement point 1001. Subsequently, in Step s202, the stimulus presentation unit 111a of the operating unit 111 displays one or a plurality of first tasks assigned to the subject 800 on the display unit 110, accepts a response or an answer to the first task by the subject 800, and sends it to the input unit 112. Here, the first task is a spatial working memory task as illustrated in FIG. 3, for example, that the positions of a plurality of white squares included in a target stimulus are memorized and retained, and after a lapse of a few seconds, the positions are recalled and determined with a probe stimulus. Subsequently, in Step s203, the stimulus presentation unit 111a of the operating unit 111 displays one or a plurality of second tasks on the display unit 110, accepts a response or an answer to the second task by the subject 800 from the input unit 112, and sends it to the analyzing unit 111c. Here, for example, the second task is a verbal working memory task requiring a phonological loop that a symbol or a character shown as a target stimulus is memorized, retained, and recalled and determined with a probe stimulus after a lapse of a few seconds as illustrated in FIG. 4. Subsequently, in Step s204, the measured control unit 111b stops acquiring biological signals from the measurement point 1001, and sends the measurement result of the biological signals to the analyzing unit 111c. Subsequently, in Step s205, the analyzing unit 111c stores the measurement result of the biological signals on the storage unit 109. Subsequently, in Step s206, based on the measurement result of the biological signals, a brain activity value Act_1 for the first task and a brain activity value Act_2 for the second task are calculated, and a mood index Mood_index is calculated as a relative value between Act_1 and Act_2 according to (Equation 2). (Equation 2) is an equation that converts the relative value between Act_1 and Act_2 into a value ranging from one to 100.

$$\text{Mood\_index} = 50 \times \left\{ 1 + \left( \frac{\text{Act\_2} - \text{Act\_1}}{|\text{Act\_2}| + |\text{Act\_1}|} \right) \right\} \quad \text{[Equation 2]}$$

Moreover, in Step s208, the stimulus presentation unit 111a displays criteria to acquire subjective information about the subject 800 as a numeric value as illustrated in FIG. 5, for example, on the display unit 110, accepts subjective information Mood_sub about the subject 800 from the input unit 112, and sends the information to the analyzing unit 111c. Here, additionally, it may be fine that the input of the subjective information is accepted in Step s208 before starting measurement in Step s201 or after calculating the mood index Mood_index in Step s206, as long as the subjective information is accepted before the subsequent Step s207. Subsequently, in Step s207, a deviation between the mood index Mood_index and the subjective information Mood_sub is calculated and displayed.

$$\text{Mood\_gap} = \text{Mood\_sub} - \text{Mood\_index} \qquad \text{[Equation 3]}$$

Figure 7:
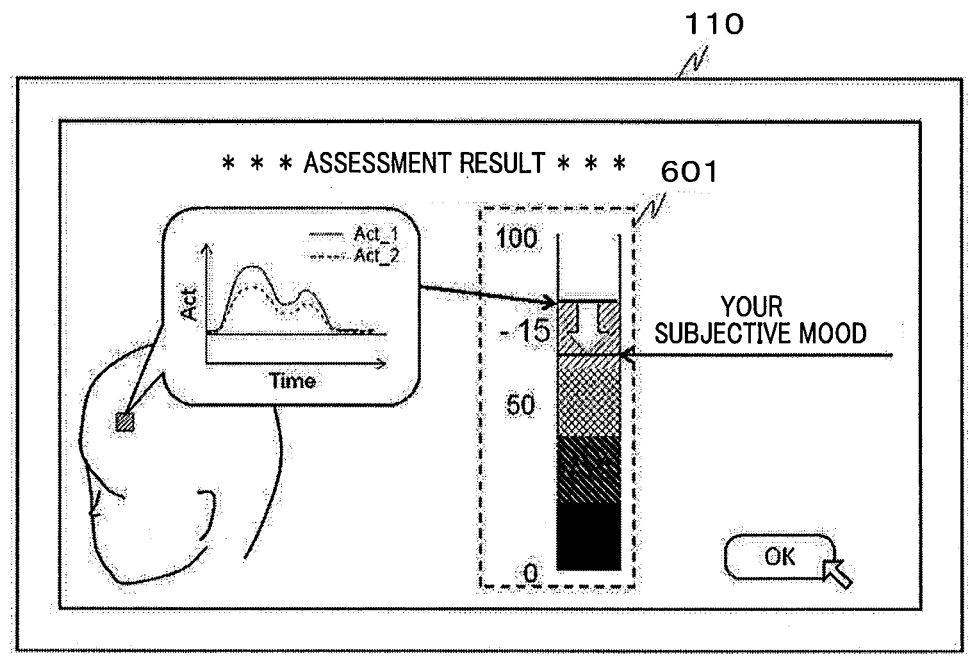
FIG. 7 is a diagram of another exemplary display of an assessment result.

Here, according to (Equation 3), for example, a gap Mood_gap between the subjective information Mood_sub and the mood index Mood_index is calculated, the mood index Mood_index and the subjective information Mood_sub are expressed on a bar 601 displayed on the display unit 110, and the numeric value of the calculated Mood_gap is displayed as illustrated in FIG. 6. Moreover, it is also possible as illustrated in FIG. 7 that the time course data of the brain activity value for the first task and the brain activity value for the second task are displayed, the mood index Mood_index and the subjective information Mood_sub are expressed on the bar 601, and the numeric value of the calculated Mood_gap is displayed.

$$\text{Mood\_gap\_r} = 100 \times \left| \frac{\text{Mood\_sub} - \text{Mood\_index}}{100} \right| \qquad \text{[Equation 4]}$$

Figure 8:
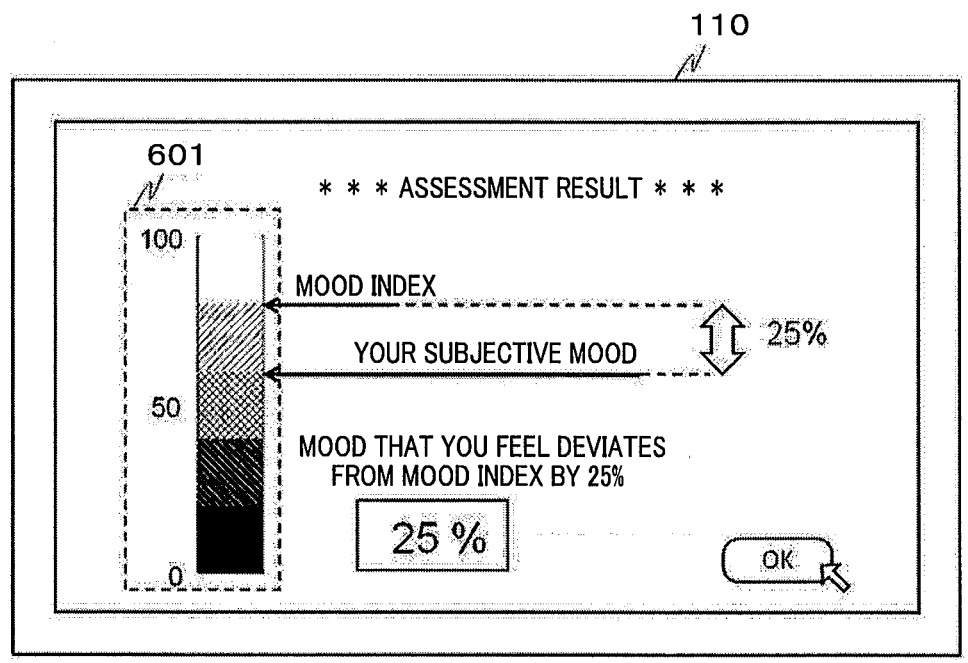
FIG. 8 is a diagram of still another exemplary display of an assessment result.
Figure 9:
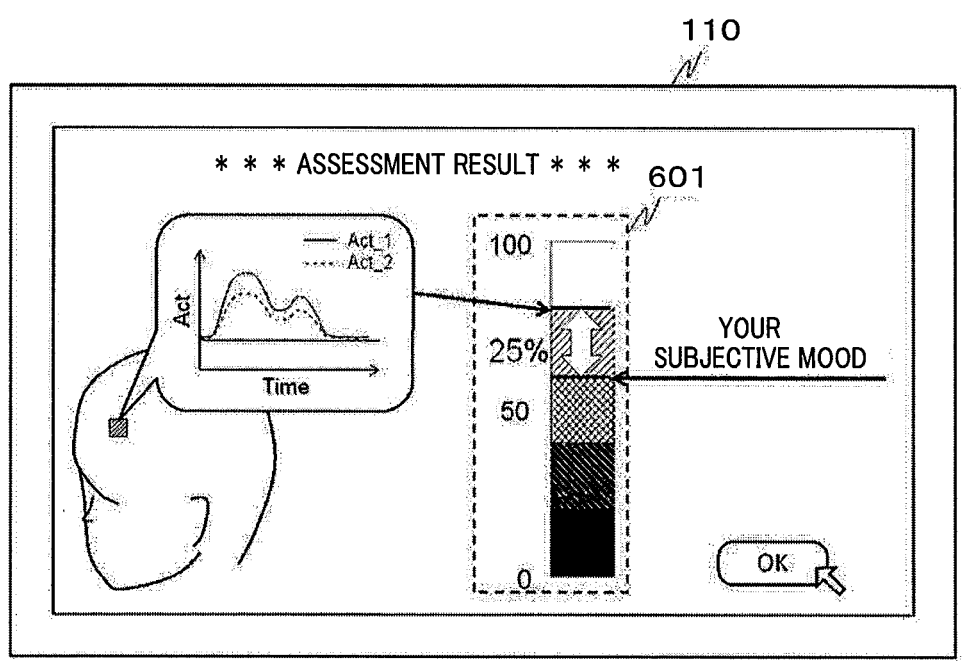
FIG. 9 is a diagram of yet another exemplary display of an assessment result.

Alternatively, a ratio Mood_gap_r of the difference between the subjective information Mood_sub and the mood index Mood_index is calculated according to (Equation 4), the mood index Mood_index and the subjective information Mood_sub are expressed on the bar 601 displayed on the display unit 110, and the numeric value of the calculated Mood_gap_r is displayed as illustrated in FIG. 8. Moreover, it is also possible as illustrated in FIG. 9 that the time course data of the brain activity value for the first task and the brain activity value for the second task are displayed, the mood index Mood_index and the subjective information Mood_sub are expressed on the bar 601, and the numeric value of the calculated Mood_gap_r is displayed.

Second Embodiment

Figure 10:
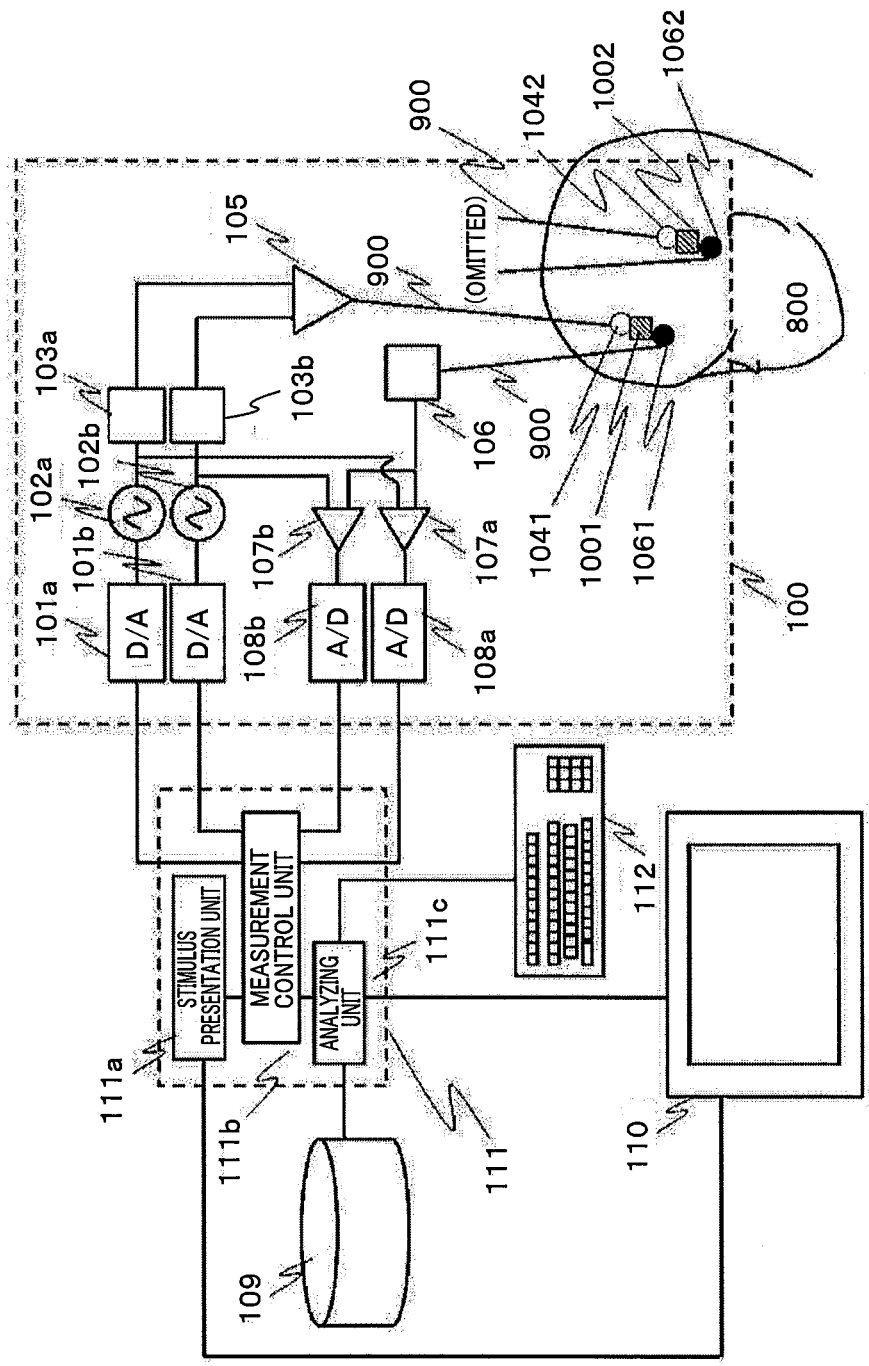
FIG. 10 is a schematic block diagram of a biological state assessment device according to a second embodiment of the present invention.

Next, FIG. 10 is a schematic block diagram of another embodiment of the biological state assessment device according to the present invention. Similarly to the schematic block diagram of the first embodiment illustrated in FIG. 1, a biological state assessment device according to this embodiment includes a biophotonic measurement unit 100 that irradiates a subject with light and detects light transmitted through or reflected off the subject for biophotonic measurement, a display unit 110 that shows a stimulus to the subject and displays a biophotonic measurement result, an operating unit 111 that shows a stimulus on the display unit 110, gives various manners of control to the biophotonic measurement unit 100, and analyzes and displays the biophotonic measurement result on the display unit 110, an input unit 112 that accepts inputs of subjective information about the subject and answers to tasks analyzed at the operating unit 111 and various items of information necessary for analysis, and a storage unit 109 that stores the biophotonic measurement result and information about the shown tasks. Here, points different from the first embodiment are in that a biophotonic measurement unit 100 includes two different irradiation units 1041 and 1042, two different light receiving units 1061 and 1062, and two measurement points 1001 and 1002 formed at nearly a middle point between a combination of the irradiation unit 1041 and the light receiving unit 1061, and at nearly a middle point between a combination of the irradiation unit 1042 and the light receiving unit 1062, respectively.

Figure 11:
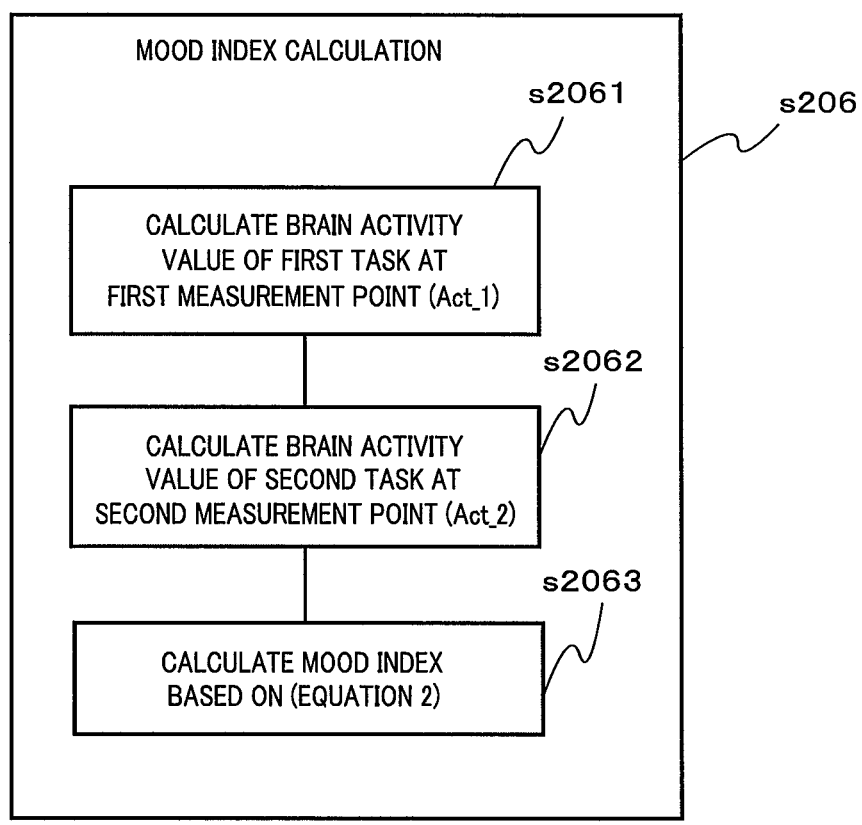
FIG. 11 is a flowchart of the process of calculating a mood index according to the second embodiment of the present invention.
Figure 12:
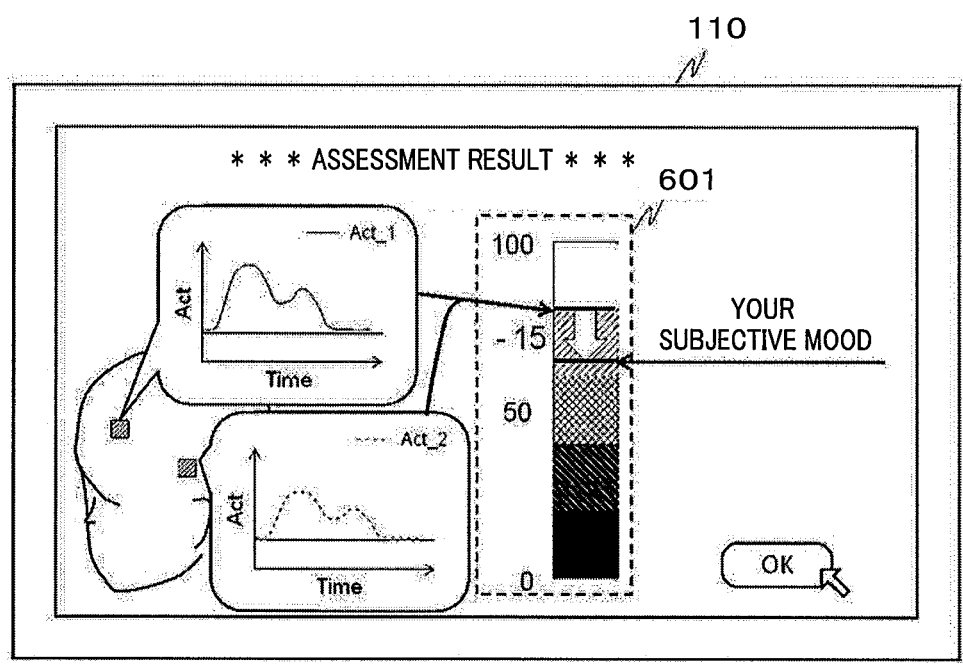
FIG. 12 is a diagram of an exemplary display of an assessment result according to the second embodiment of the present invention.

In the embodiment, similarly to the first embodiment, in carrying out processes according to the flowchart illustrated in FIG. 2, FIG. 11 is the detail of calculation in Step s206 more specifically. In Step s206, first, in Step s2061, the brain activity value Act_1 for the first task is calculated at the first measurement point 1001, and then in Step s2062, the brain activity value Act_2 for the second task is calculated at the second measurement point 1002. Subsequently, in Step s2063, the mood index Mood_index is calculated for the relative value between Act_1 and Act_2 at two different measurement points using Act_1 and Act_2 calculated in Steps s2061 and s2062 according to (Equation 2) described above. This is similar to the first embodiment in that Mood_gap and Mood_gap_r are calculated and displayed using the calculated Mood_index. Moreover, it is also possible as in FIG. 12 that the time course data of the brain activity value for the first task at the first measurement point 1001 and the brain activity value for the second task at the second measurement point 1002 are displayed, the mood index Mood_index and the subjective information Mood_sub are expressed on the bar 601, and the numeric value of the calculated Mood_gap is displayed.

Third Embodiment

Figure 13:
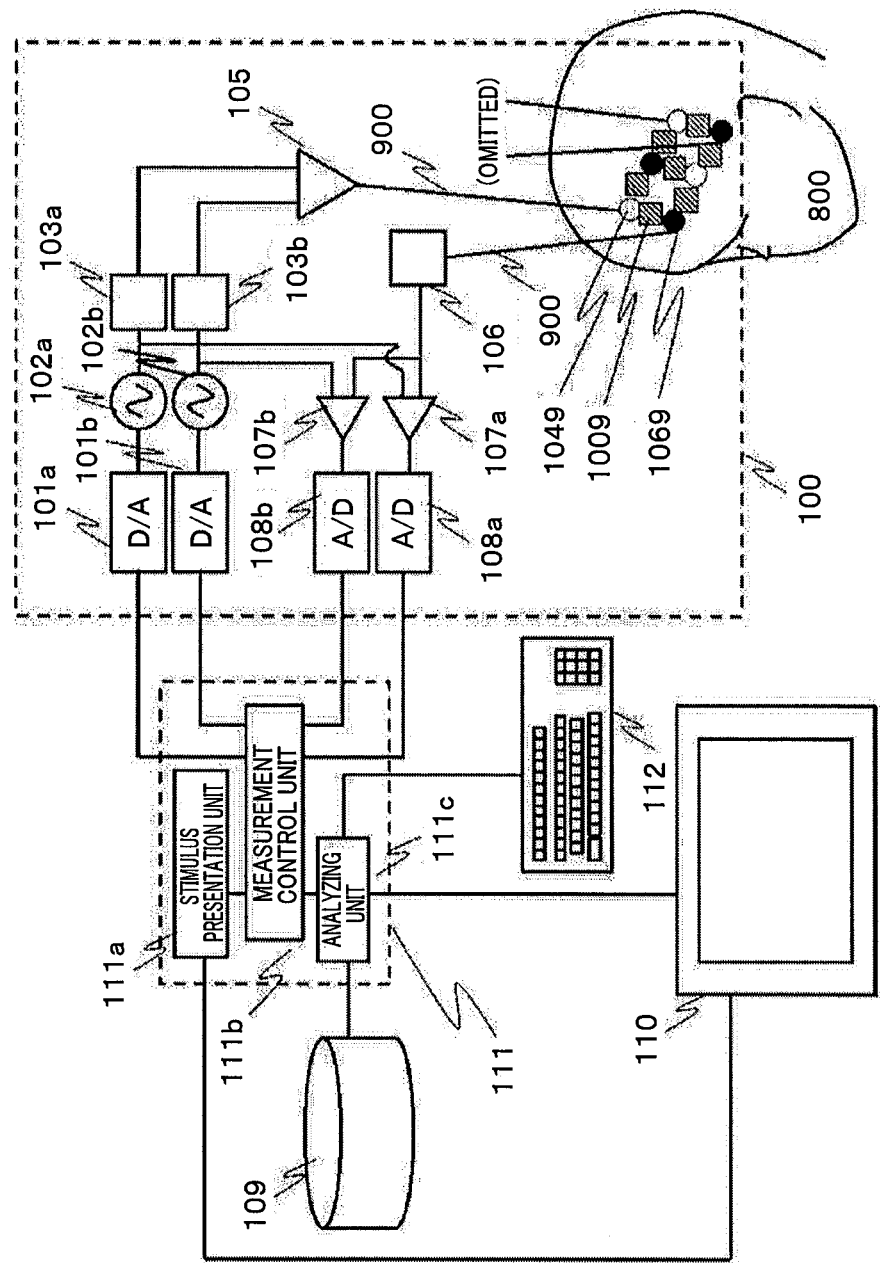
FIG. 13 is a schematic block diagram of a biological state assessment device according to a third embodiment of the present invention.
Figure 14:
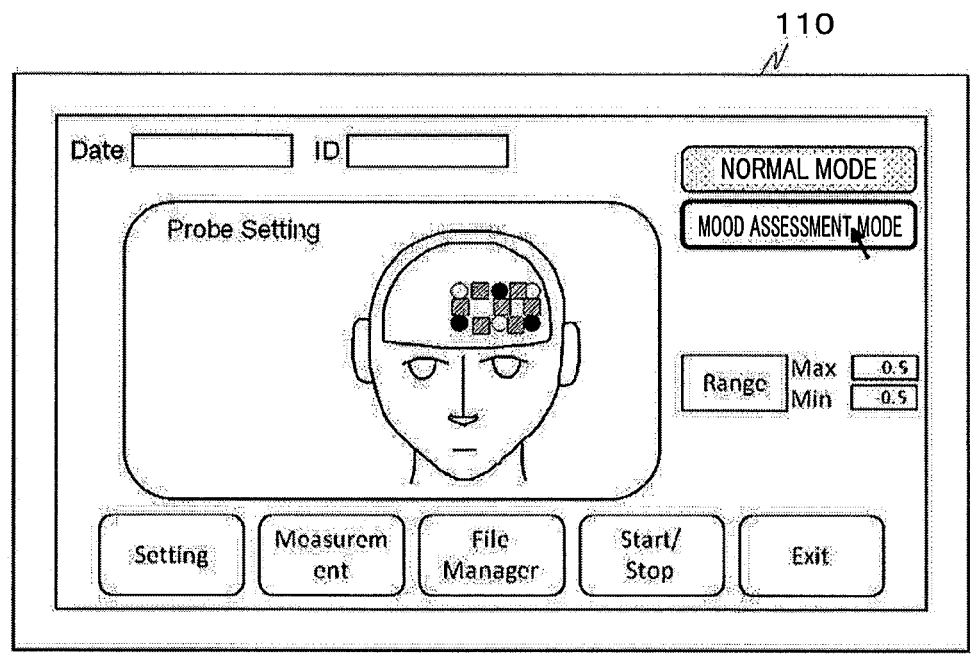
FIG. 14 is a diagram of an exemplary display for selecting a mode according to the third embodiment of the present invention.
Figure 15:
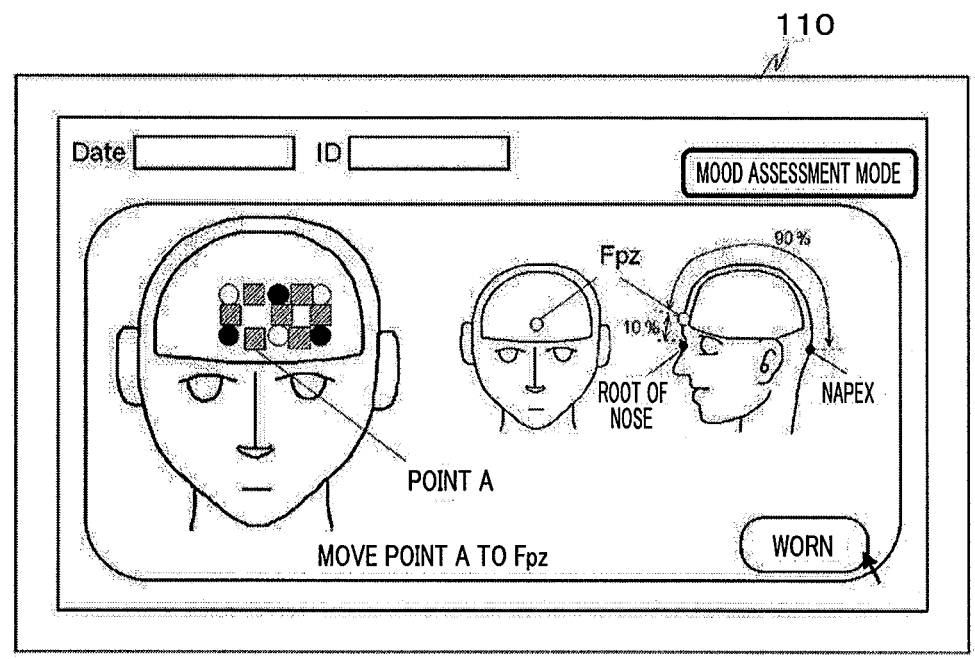
FIG. 15 is a diagram of an exemplary display of a teaching screen according to the third embodiment of the present invention.
Figure 16:
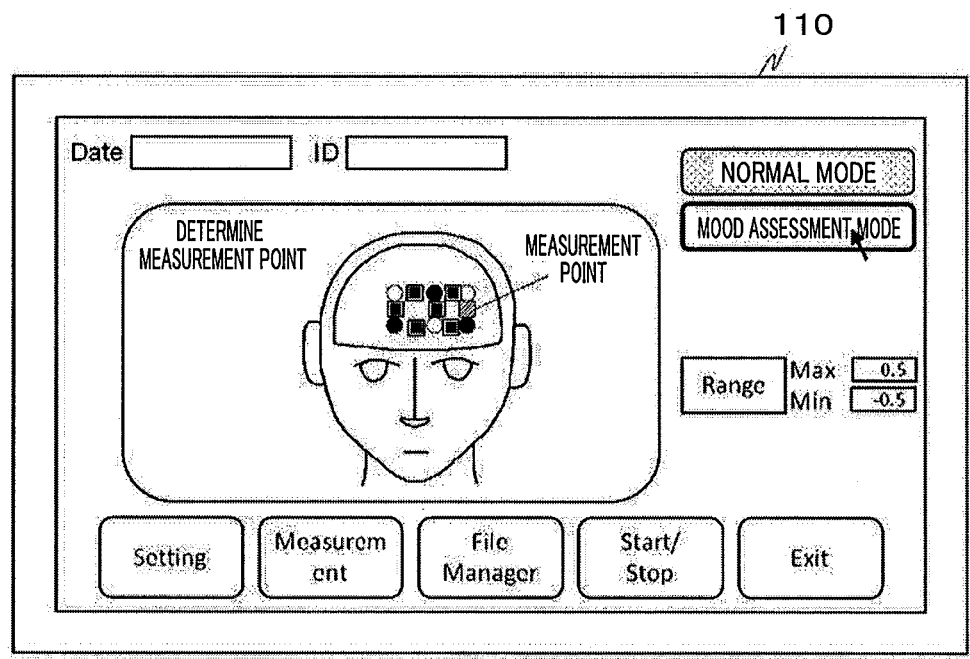
FIG. 16 is a diagram of an exemplary display of a measurement point according to the third embodiment of the present invention.
Figure 17:
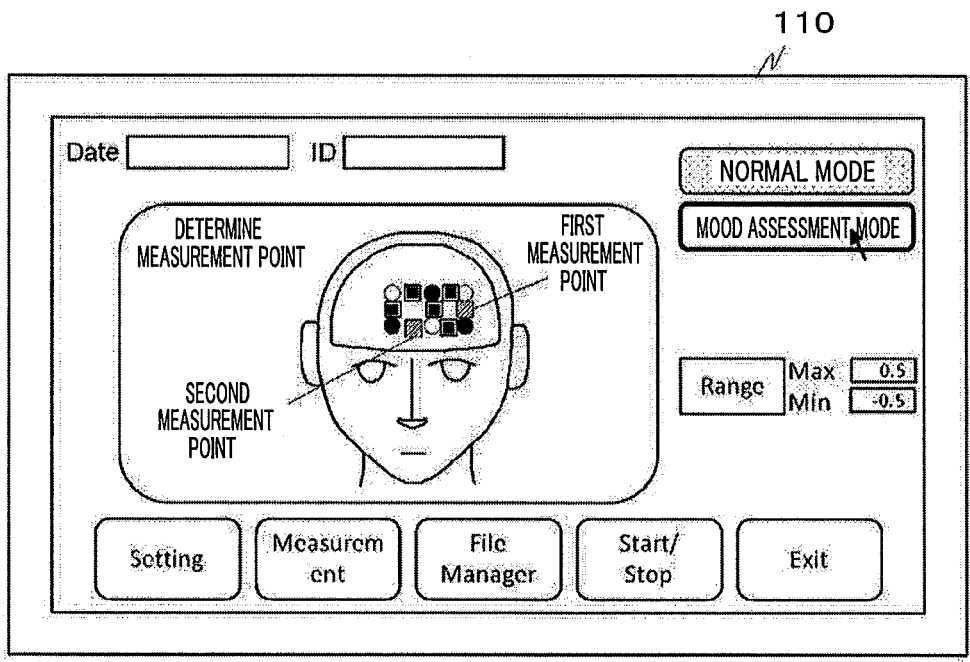
FIG. 17 is a diagram of another exemplary display of a measurement point according to the third embodiment of the present invention.

Next, FIG. 13 is an example that a biological state assessment device is implemented by installing a program according to the present invention on a biophotonic measurement device including a plurality of irradiation units 1049, a plurality of light receiving units 1069, and a plurality of measurement points 1009 formed at nearly a middle point between the irradiation units 1049 and the light receiving units 106 in a plurality of combinations of the irradiation units 1049 and the light receiving units 1069. In the embodiment, in a typical biophotonic measurement device that acquires biological signals at the plurality of the measurement points 1009, more specifically, software that calculates the mood index Mood_index, Mood_gap, and Mood_gap_r described in the first and second embodiments is installed on an operating unit 111. In the embodiment, the program installed on the operating unit 111 performs the following operation. First, for example, as illustrated in FIG. 14, a stimulus presentation unit 111a selectively displays "a normal mode" (the operation as the biophotonic measurement device) that a normal biological signal is acquired and "a mood assessment mode" (the operation as the biological state assessment device) that the mood index Mood_index, for example, on a display unit 110. The operating unit 111 accepts a selection of "the mood assessment mode" through an input unit 112 such as a keyboard, a controller, and a mouse, and then displays a teaching screen for wearing the irradiation units 1049, the light receiving units 1069, and the measurement points 1009 on a subject 800 on the display unit 110 as illustrated in FIG. 15. The operating unit 111 accepts the completion of wearing from the input unit 112, and then shows places corresponding to the measurement point 1001 in the first embodiment, for example, in a plurality of the measurement points 1009 as illustrated in FIG. 16. Alternatively, the operating unit 111 shows places corresponding to the first measurement point 1001 and the second measurement point 1002 in the second embodiment, for example, in the plurality of the measurement points 1009 as illustrated in FIG. 17. After that, according to the procedures described in the first or second embodiment, Mood_index, Mood_gap, and Mood_gap_r are calculated and displayed. In the embodiment, in the plurality of the irradiation units 1049 and the plurality of the light receiving units 1069 of the biophotonic measurement device, it is possible to use only the irradiation unit and the light receiving unit necessary to measure the measurement point 1001 or 1002. As described above, the program according to the present invention is installed, so that it is possible to implement measurement similar to the first or second embodiment in the biophotonic measurement device including the plurality of the measurement points 1009.

Fourth Embodiment

Figures 18, 19:
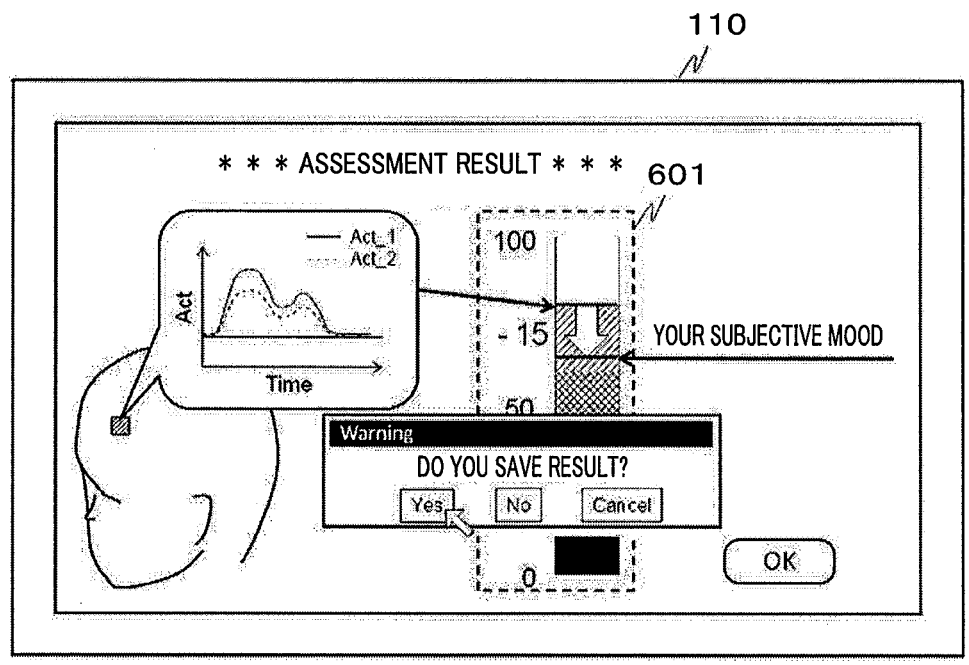
FIG. 18 is a diagram of an exemplary display for making a selection to save an assessment result according a fourth embodiment to the present invention.
FIG. 19 is a diagram of an exemplary table to be stored on a storage unit.

In the biological state assessment devices according to the first to third embodiments, a measured result and an analysis result can be saved. For example, as illustrated in FIG. 7, after results are displayed on a display unit 110, after a certain period of time, or after a selection of "OK" is accepted at the input unit 112, as illustrated in FIG. 18, a screen to select whether the results are saved is displayed on the display unit 110. Here, the operating unit 111 accepts a selection of "Yes" through the input unit 112, and stores a measured result and an analysis result on the storage unit 109. On the storage unit 109, for example as illustrated in FIG. 19, a subject ID, a measured date and time, the brain activity value Act_1 for the first task, the brain activity value Act_2 for the second task, the mood index Mood_index, and the subjective information Mood_sub are stored on a table 1901 in association with one another. Moreover, it is also possible that the operating unit 111 automatically stores the results on the storage unit 109 without the display of the selection screen to save the result as illustrated in FIG. 18.

Fifth Embodiment

Figure 20:
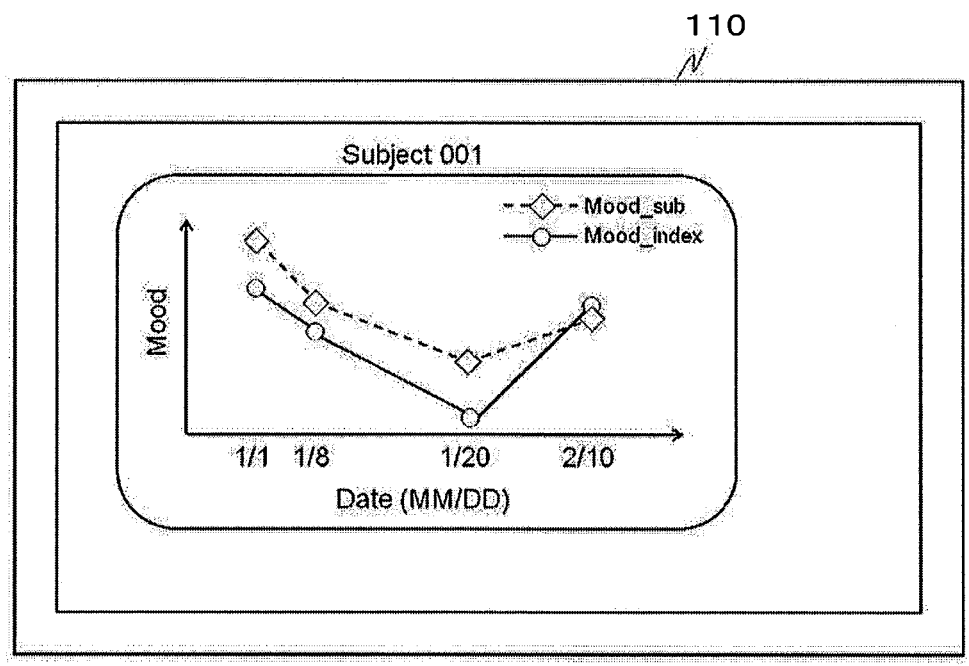
FIG. 20 is a diagram of an exemplary display of changes over time according to a fifth embodiment of the present invention.

Next, in the device configurations according to the first and second embodiments and the device configuration and the software according to the third embodiment, an example is shown in which changes over time are displayed including the past measured results. A biological state assessment device according to this embodiment acquires the mood index Mood_index and the subjective information Mood_sub according to the flowchart illustrated in FIG. 2 similarly to the first to third embodiments. After that, the operating unit 111 reads Mood_index and Mood_sub acquired and stored on the storage unit 109 in the past from the table 1901, illustrated in FIG. 19, for example, and displays them on the display unit 110 together with Mood_index and Mood_sub newly acquired as a time series graph illustrated in FIG. 20, for example. As described above, the mood index and subjective information from the past to the present time are visualized, so that it is possible to feed back changes in them and manners of deviation to the subject.

Sixth Embodiment

Figure 21:
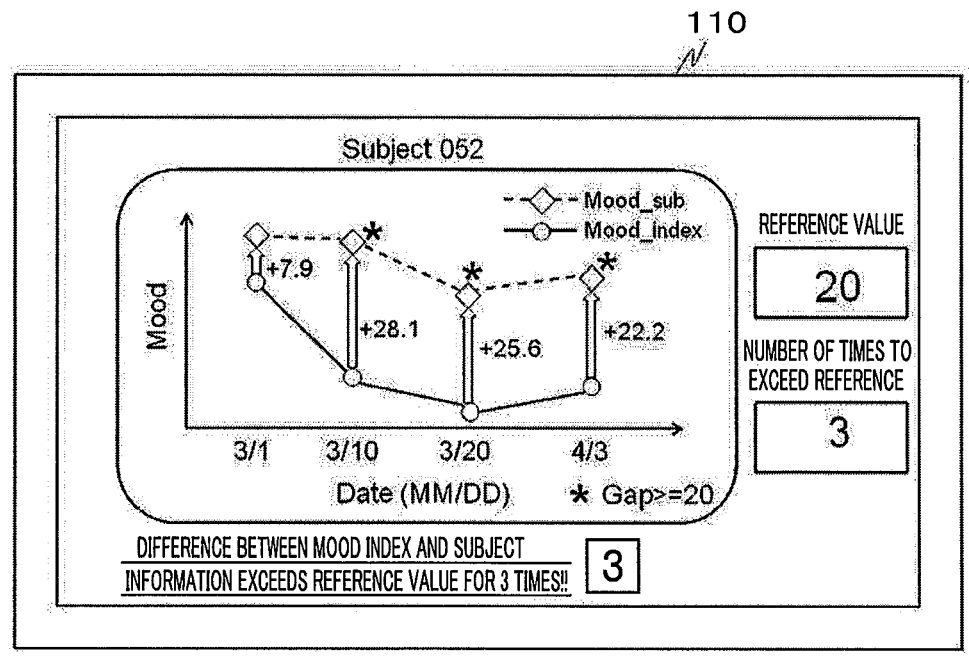
FIG. 21 is a diagram of an exemplary display according to a sixth embodiment of the present invention.

Next, in an example in which changes over time are displayed including the past measured results in the device configuration and the software according to the fifth embodiment, an example is shown in which a warning is displayed in the case where the number of times that the absolute value of the difference between Mood_index and Mood_sub is a certain value ref_val or greater is continued for N times or greater. In the embodiment, similarly to the fifth embodiment, the operating unit 111 reads Mood_index and Mood_sub acquired and stored on the storage unit 109 in the past, as illustrated in FIG. 21, and displays them on the display unit 110 together with Mood_index and Mood_sub newly acquired as a time series graph. Moreover, the differences between Mood_index and Mood_sub on measurement days are calculated, and differences on the measurement days are displayed. Furthermore, simultaneously with this, the operating unit 111 determines that a day on which the calculated absolute value of the difference between the measurement days is ref_val or greater, and displays a warning message in the case where this is continued for N times or greater. More specifically, FIG. 21 is an example of ref_val=20 and N=3. According to the embodiment, it is possible to point out the deviation of the state that the subject him/herself subjectively feels from the mood in him/herself and to cause the subject him/herself to be aware of the deviation. Moreover, it is without saying that the operating unit 111 can calculate the difference between Mood_index and Mood_sub calculated here beforehand and store the difference on the storage unit 109. The difference can be stored in association with one another as one row is additionally provided on the table 1901 illustrated in FIG. 19, for example.

Seventh Embodiment

Figure 22:
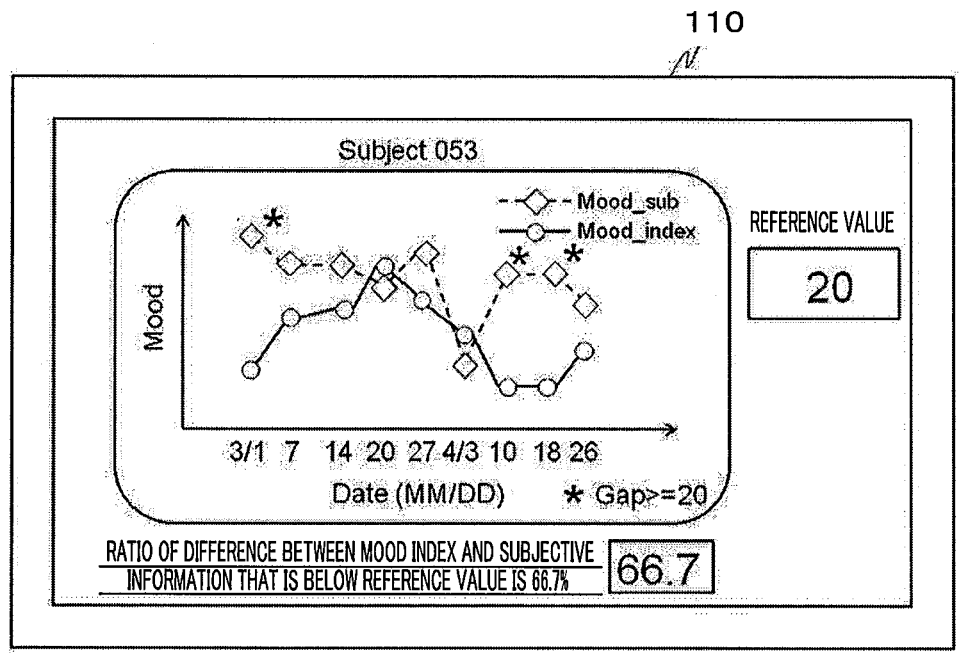
FIG. 22 is a diagram of an exemplary display according to a seventh embodiment of the present invention.

Next, in an example in which changes over time are displayed including the past measured results in the device configuration and the software according to the fifth embodiment, an example is shown in which a ratio that the absolute value of the difference between Mood_index and Mood_sub is a certain value ref_val or less is displayed. In the embodiment, the operating unit 111 reads Mood_index and Mood_sub acquired and stored on the storage unit 109 in the past. Here, for example, in the case where ref_val=20, as illustrated in FIG. 22, the operating unit 111 displays them on the display unit 110 together with Mood_index and Mood_sub newly acquired as a time series graph, calculates the differences between Mood_index and Mood_sub on measurement days, gives an asterisk, for example, to a day on which the difference is rev_val or greater, for example, and displays the days on the display unit 110. Moreover, the operating unit 111 calculates a ratio that the measurement days on which the difference is less than rev_val are occupied in all the measurement days, and displays the ratio on the display unit 110. The example in FIG. 22 illustrates the ratio is 66.7% because the number of times of the measurement days on which the value ref_val is 20 or less is six with respect to the total number of times of measurement that is nine times. According to the embodiment, it is possible to point out how much the state that the subject him/herself subjectively feels is matched with the mood in him/herself and to cause the subject him/herself to be aware of the deviation.

Eighth Embodiment

Figure 23:
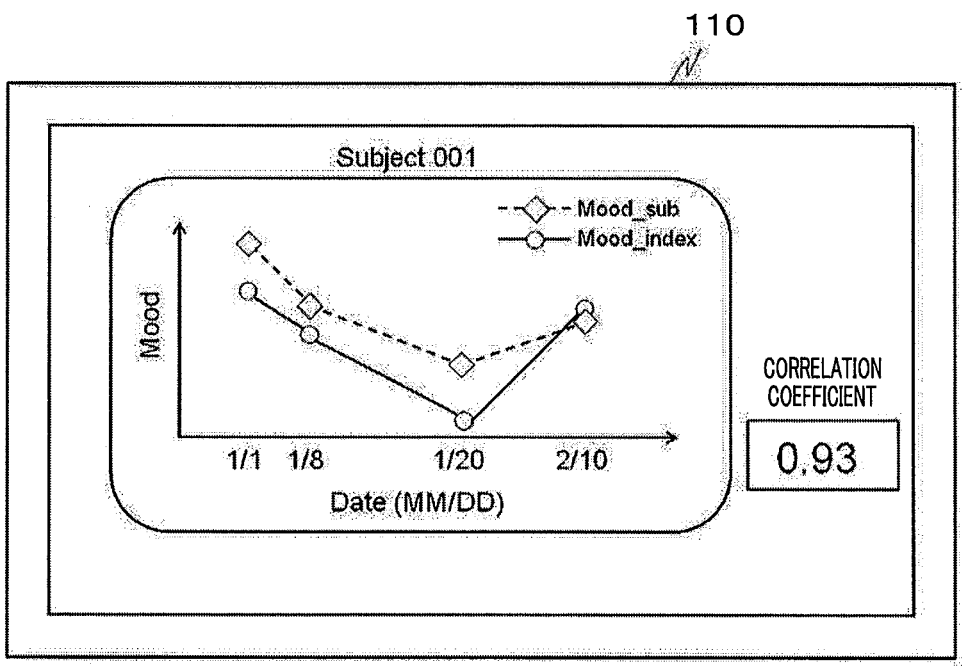
FIG. 23 is a diagram of an exemplary display according to an eighth embodiment of the present invention.

Next, in an example in which changes over time are displayed including the past measured results in the device configuration and the software according to the fifth embodiment, an example is shown in which the correlation between Mood_index and Mood_sub is displayed. In the embodiment, as illustrated in FIG. 23, for example, the operating unit 111 reads Mood_index and Mood_sub acquired and stored on the storage unit 109 in the past, displays them on the display unit 110 together with Mood_index and Mood_sub newly acquired, calculates the correlation coefficient of time series data between Mood_index and Mood_sub, and displays the correlation coefficient on the display unit 110. It may be fine that the correlation coefficient calculated here is Spearman's rank correlation coefficient in the case where specific distributions are not assumed for Mood_index and Mood_sub. According to the embodiment, the correlation between Mood_index and Mood_sub is visualized, so that it is possible to express that changes in the state that the subject him/herself subjectively feels have a tendency how much the changes are close to changes in the mood in him/herself.

Ninth Embodiment

Figure 24:
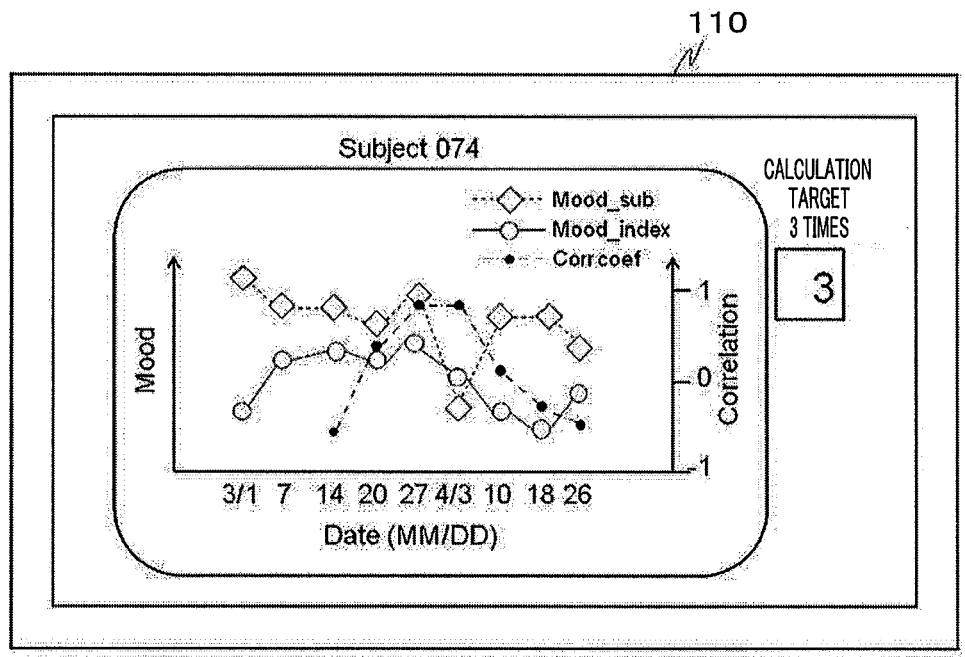
FIG. 24 is a diagram of an exemplary display according to a ninth embodiment of the present invention.

Next, in an example in which changes over time are displayed including the past measured results in the device configuration and the software according to the fifth embodiment, an example is shown in which M correlations between Mood_index and Mood_sub in the past are calculated and displayed. In FIG. 24, an example is shown where M=3. In the embodiment, the operating unit 111 reads Mood_index and Mood_sub acquired and stored on the storage unit 109 in the past, forms them into items of time series data together with Mood_index and Mood_sub newly acquired, displays the items of data on the display unit 110, and calculates M correlation coefficients between Mood_index and Mood_sub in the past (M=3 in FIG. 24). In the case where both of Mood_index and Mood_sub include data of M+1 correlation coefficients or greater, the correlation coefficient can also be expressed as time series data. As illustrated in FIG. 24, for example, two vertical axes are provided, one is assigned to Mood_index and Mood_sub, the other is assigned to the correlation coefficient, and Mood_index, Mood_sub, and changes in the correlation coefficients are plotted on the same graph on the display unit 110. According to the embodiment, it is possible to visualize how much the tendency of the correlation between them is varied over time in addition to the state that the subject him/herself subjectively feels and the mood in him/herself.

Tenth Embodiment

Figure 25:
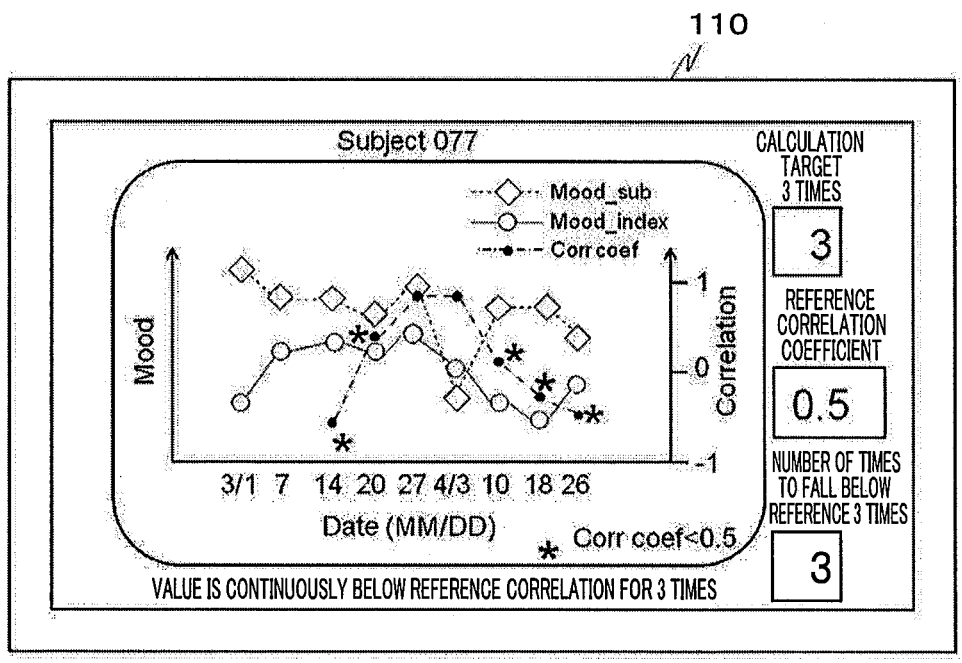
FIG. 25 is a diagram of an exemplary display according to a tenth embodiment of the present invention.

Next, in an example in which in the device configuration and the software according to the ninth embodiment, changes over time are calculated and displayed including the past measured results and M correlations in the past, an example is shown in which a warning is displayed in the case where the number of times that values fall below a certain correlation coefficient ref_corr is continued for N times or greater. FIG. 25 is an example where M=3, ref_corr=0.5, and N=3. For example, in time series data of M correlation coefficients in the past (in FIG. 25, M=3 similarly to the ninth embodiment), the operating unit 111 gives an asterisk, for example, to data below ref_corr (0.5 here), and displays the data on the display unit 110, and a warning message is displayed on the display unit 110 in the case where the correlation coefficient continuously falls below ref_corr for N times (N=3 here). According to the embodiment, it is possible to point out how the state that the subject him/herself subjectively feels is matched with the mood in him/herself and how they deviate from each other and to cause the subject him/herself to be aware of the deviation.

Eleventh Embodiment

In the device configuration of the biological state assessment device according to the first embodiment, it may be fine that the optical mixer 105 and the optical fiber bundles 900 are not included in the device configuration and the irradiation unit 1041 is configured to incorporate the light sources 103a and 103b. Moreover, in the device configuration of the biological state assessment device according to the first embodiment, it may be fine that the optical fiber bundles 900 is not included in the device configuration and the light receiving unit 1061 is configured to incorporate the detector 106. Moreover, similarly, it may be fine that in the second and third embodiments, the irradiation units are configured to incorporate the light sources, and the light receiving units are configured to incorporate the detector.

Twelfth Embodiment

Figure 26:
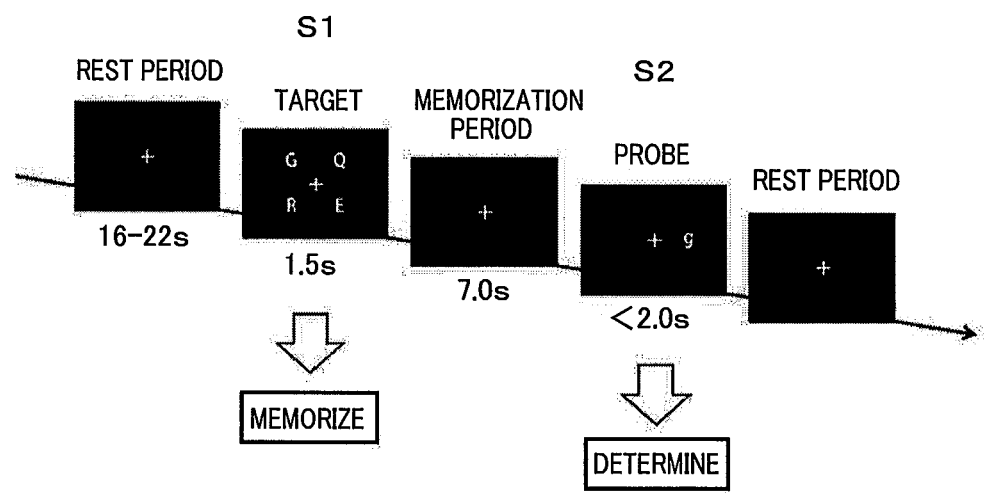
FIG. 26 is a diagram of another exemplary verbal working memory task.
Figure 27:
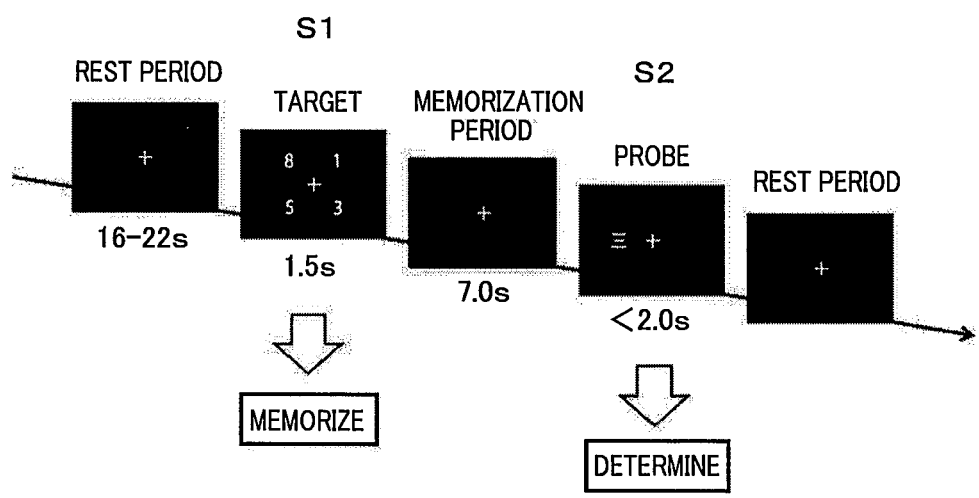
FIG. 27 is a diagram of another exemplary verbal working memory task.

In the device configuration and the software according to all the embodiments described above, FIG. 26 is an example of a verbal working memory task using an alphabet instead of the verbal working memory task illustrated in FIG. 4. Moreover, FIG. 27 is an example of a verbal working memory task using Arabic numerals and a Kanji character instead of the verbal working memory task illustrated in FIG. 4. According to the embodiment, it is possible to configure a device and software similar to all the embodiments described above also for a subject more familiar with an alphabet than Japanese language and a subject more familiar with Kanji characters than Japanese language.

Thirteenth Embodiment

It is also possible that in the calculation of the mood index Mood_index in all the embodiments described above, the brain activity value Act_1 for the first task and the brain activity value Act_2 for the second task are multiplied by weight coefficients k1 and k2, respectively, and calculated according to (Equation 5) instead of (Equation 2) described above. Moreover, similarly, it is also possible that Act_1 and Act_2 are multiplied by weight coefficients k1 and k2, respectively, and converted into values ranging from one to 100 according to (Equation 6).

$$\text{Mood\_index} = \frac{k_2 \times \text{Act\_2} - k_1 \times \text{Act\_1}}{|k_2 \times \text{Act\_2}| + |k_1 \times \text{Act\_1}|} \qquad \text{[Equation 5]}$$

$$\text{Mood\_index} = 50 \times \left\{1 + \left(\frac{k_2 \times \text{Act\_2} - k_1 \times \text{Act\_1}}{|k_2 \times \text{Act\_2}| + |k_1 \times \text{Act\_1}|}\right)\right\} \qquad \text{[Equation 6]}$$

Fourteenth Embodiment

Figure 28:
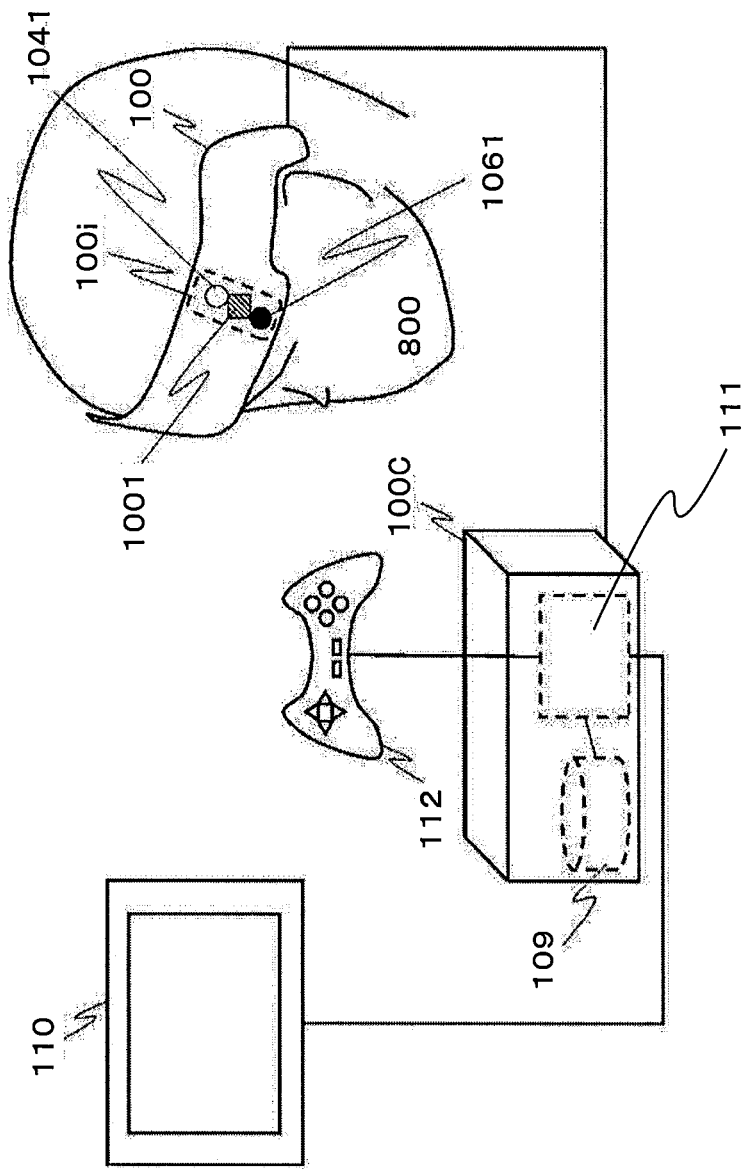
FIG. 28 is a diagram of the schematic configuration of a biological state assessment device according to a fourteenth embodiment of the present invention.

Next, FIG. 28 is an exemplary biological state assessment device according to the present invention. As illustrated in FIG. 28, a biophotonic measurement unit 100 has a shape to be worn on all or a part of the forehead of a subject 800, and includes an irradiation point 1041, a light receiving unit 1061, and a measurement point 1001 formed of combinations of the irradiation unit 1041 and the light receiving unit 1061 on a certain region 100i on the inner surface facing the subject 800 in the biophotonic measurement unit 100. Moreover, an operating unit 111 and a storage unit 109 are incorporated in a cabinet 100C, connected to a display unit 110, an input unit 112, and the biophotonic measurement unit 100, and can perform processes similar to the processes in all the embodiments described above.

Fifteenth Embodiment

Figure 29:
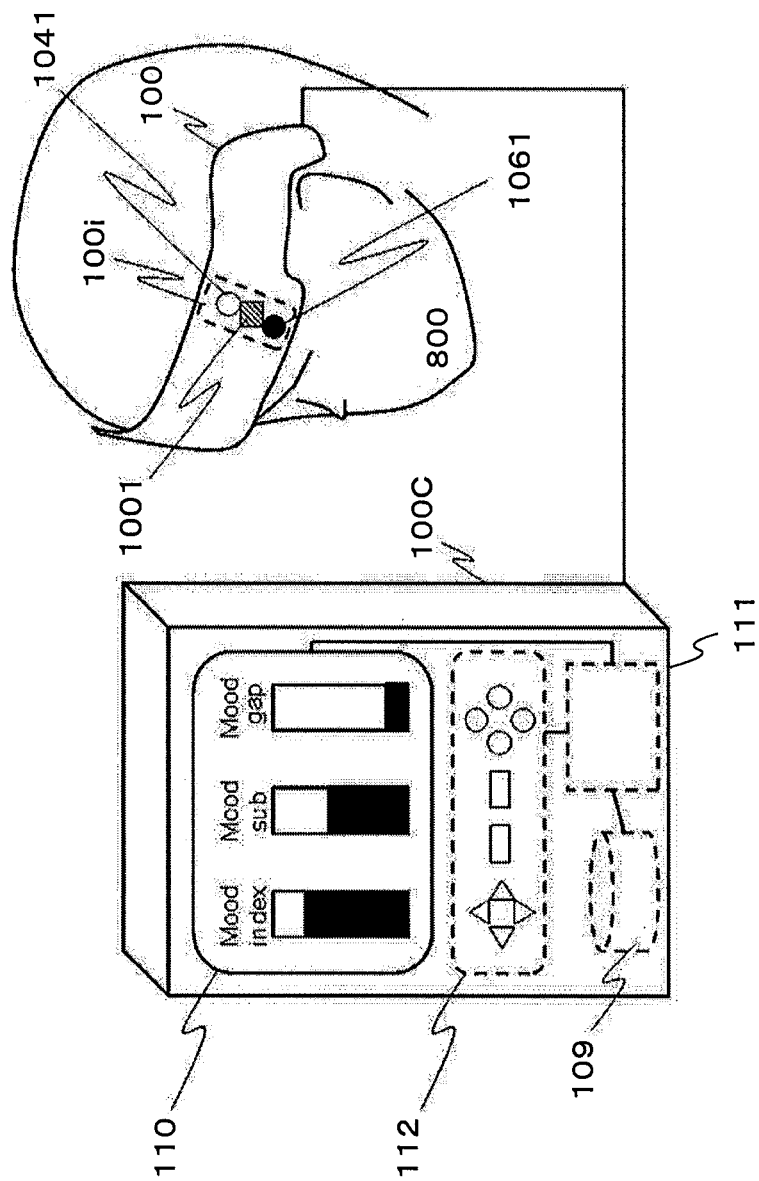
FIG. 29 is a diagram of the schematic configuration of a biological state assessment device according to a fifteenth embodiment of the present invention.

The biological state assessment device according to the fourteenth embodiment can integrate the storage unit 109, the display unit 110, the operating unit 111, and the input unit 112 in a single cabinet 100C. FIG. 29 is a part of this embodiment. The storage unit 109 and the operating unit 111 are incorporated in the cabinet 100C, and the display unit 110 and the input unit 112 are integrated in such a form in which the display unit 110 and the input unit 112 are partially exposed to the surface of the cabinet 100C. Moreover, FIG. 29 is an example of display on the display unit 110, and the mood index Mood_index, the subjective information Mood_sub, and Mood_gap that is the difference between both are plotted and displayed in bars. As described above, it is possible to implement biophotonic measurement and the display of results in a compact form as a device.

LIST OF REFERENCE SIGNS 100 biophotonic measurement unit
100C cabinet
100i region including the irradiation unit, the light receiving unit, and the measurement point on the inner surface of the biophotonic measurement unit 100
1001 first measurement point
1002 second measurement point
101a, 101b digital analog converter
102a, 102b modulator
103a, 103b light source
105 optical mixer
1041, 1042 irradiation unit
106 detector
1061, 1062 light receiving unit
107a, 107b lock-in amplifier
108a, 108b analog digital converter
109 storage unit
110 display unit
111 operating unit
111a stimulus presentation unit
111b measurement control unit
111c analyzing unit
112 input unit
1901 table
601 region showing a color bar on the display unit 110
800 subject
900 optical fiber bundles

The invention claimed is:

1. A biological state assessment device comprising:
one or more first light sources that emit light at different wavelengths, a first optical mixer that mixes the light emitted from the first light sources, a first optical fiber bundle that guides the light mixed at the optical mixer;
a photodetector configured to detect light, which is emitted from the one or more first light sources, transmitted through or reflected off a subject;
a display unit configured to display a plurality of different tasks to the subject;
a storage unit;
an input unit, which is one of a mouse, a keyboard, and a controller, configured to accept an input of information;
a computer connected to each of the one or more first light sources, the photodetector, the display unit, and the storage unit, programmed to:
send signals to drive the first light sources to emit the light,
while the light is being emitted by the first light sources, control the photodetector to detect light, control the display unit to display a first task of the plurality of different tasks, control the input unit to receive first input information in response to the displayed first task, acquire a first time series of data from the photodetector relating to the first task and store the acquired first time series of data in the storage unit, control the display unit to display a second task of the plurality of different tasks, which is different than the first task, control the input unit to receive second input information in response to the displayed second task, acquire a second time series of data from the photodetector related to the second tasks and store the acquired second time series of data in the storage unit, store the respective responses in the storage unit,
stop sending signals to drive the light sources to emit the light,
control the display unit to display a screen prompting the subject to input third input information which indicates an emotion of the subject and control the input unit to acquire the third input information,
calculate a first brain activity value based on the first time series of data and calculate a second brain activity value based on the second time series of data,
calculate a relative value indicating an emotion of the subject, according to the equation: $(Act\_2-Act\_1)/(|Act\_2|+|Act\_1|)$, wherein $Act\_1$ is the first brain activity value and $Act\_2$ is the second brain activity value,
store previously calculated relative value based on previously acquired first time series of data and previously acquired second time series of data measured at a time interval,
store previously acquired third input information indicating an emotion of the subject at the time interval,
determine if absolute values of differences between the previously calculated relative value and the previously acquired third input information in a same time interval are greater than or equal to a first predetermined value,
determine if the absolute values of differences are greater than the predetermined value for a second predetermined value of consecutive time intervals, and
control the display unit to simultaneously display, in a screen of the display:
a first time series of the relative value and previously calculated relative values, a second time series of the acquired third input information and previously acquired third input information, a numerical indication of the absolute values of differences between the previously calculated relative values and the previously acquired third input information in the same time intervals, and
a warning message if the absolute values of differences are greater than the predetermined value for the second predetermined value of consecutive time intervals,
wherein the first task is a spatial memory task and the second task is a verbal memory task.

2. The biological state assessment device according to claim 1, further comprising:
one or more second light sources that emit light at different wavelengths ranging from 600 to 900 nm, a second optical mixer that mixes the light emitted from the second light sources, a second optical fiber bundle that guides the light mixed at the optical mixer,
wherein the photodetector detects light, which is emitted from the one or more first light sources and the one or more second light sources, transmitted through or reflected off the subject, wherein the computer is further configured to:
send signals to drive the first light sources to emit the light and the second light sources to emit light,
while the light is being emitted by the first and second light sources, control the photodetector to detect light received at the receiving unit at the first measurement point, control the photodetector to detect light received at the receiving unit at the second measurement point, control the display unit to display a first task of the plurality of different tasks, control the input unit to receive first input information in response to the displayed first task, acquire a first time series of data from the photodetector relating to the first task and store the acquired first time series of data in the storage unit, display a second task of the plurality of different tasks, which is different than the first task, control the input unit to receive second input information in response to the displayed second task, acquire a second time series of data from the photodetector related to the second task and store the acquired second time series of data in the storage unit, store the respective responses in the storage unit.

3. The biological state assessment device according to claim 1,
wherein the computer further calculates a correlation coefficient between the relative value and the third input information including a measured result acquired in a past and graphically displays the correlation coefficient on the display unit.

4. The biological state assessment device according to claim 1,
wherein the computer further calculates a correlation coefficient for a specific number of times between the relative value and the third input information including a measured result acquired in a past, and displays changes over time in the correlation coefficient.

* * * * *